(12) United States Patent
Quevy et al.

(10) Patent No.: US 11,921,077 B2
(45) Date of Patent: *Mar. 5, 2024

(54) ALL-ELECTRONIC HIGH-THROUGHPUT ANALYTE DETECTION SYSTEM

(71) Applicant: ProbiusDx, Inc., Sunnyvale, CA (US)

(72) Inventors: Emmanuel Philippe Quevy, El Cerrito, CA (US); Chaitanya Gupta, Redwood City, CA (US); Jeremy Hui, San Francisco, CA (US)

(73) Assignee: ProbiusDx, Inc., El Cerrito, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/358,909

(22) Filed: Jun. 25, 2021

(65) Prior Publication Data

US 2022/0057357 A1    Feb. 24, 2022

Related U.S. Application Data

(63) Continuation of application No. 16/194,208, filed on Nov. 16, 2018, now Pat. No. 11,054,380.
(Continued)

(51) Int. Cl.
*G01N 27/404*    (2006.01)
*G01N 27/327*    (2006.01)
*G01N 33/483*    (2006.01)

(52) U.S. Cl.
CPC ..... *G01N 27/4045* (2013.01); *G01N 27/3273* (2013.01); *G01N 33/4836* (2013.01)

(58) Field of Classification Search
CPC ........... G01N 27/4045; G01N 27/3273; G01N 27/27; G01N 27/416; G01N 27/4166; G01N 33/4836
See application file for complete search history.

(56) References Cited

U.S. PATENT DOCUMENTS 6,915,168 B1    7/2005    Benz et al.
7,572,355 B1    8/2009    Arumugam et al.
(Continued)

FOREIGN PATENT DOCUMENTS

DE    10 2013 004204 A1    9/2014
WO    WO-2014/139494 A1    9/2014
(Continued)

OTHER PUBLICATIONS

U.S. Appl. No. 62/328,798, filed Apr. 28, 2016 (Year: 2016).*
(Continued)

*Primary Examiner* — Alexander S Noguerola
(74) *Attorney, Agent, or Firm* — Mintz Levin Cohn Ferris Glovsky and Popeo, P.C.

(57) ABSTRACT

An all-electronic high-throughput detection system can perform multiple detections of one or more analyte in parallel. The detection system is modular, and can be easily integrated with existing microtiter plate technologies, automated test equipments and lab workflows (e.g., sample handling/distribution systems). The detection system includes multiple sensing modules that can perform separate analyte detection. A sensing module includes a platform configured to couple to a sample well. The sensing module also includes a sensor coupled to the platform. The sensing module further includes a first electrode coupled to the platform. The first electrode is configured to electrically connect with the sensor via a feedback circuit. The feedback circuit is configured to provide a feedback signal via the first electrode to a sample received in the sample well, the feedback signal based on a potential of the received sample detected via a second electrode.

8 Claims, 19 Drawing Sheets

Related U.S. Application Data

(60) Provisional application No. 62/587,889, filed on Nov. 17, 2017.

(56) References Cited

U.S. PATENT DOCUMENTS

| | | |
|---|---|---|
| 9,285,336 B2 | 3/2016 | Gupta |
| 10,101,293 B2 | 10/2018 | Gupta |
| 11,054,380 B2 | 7/2021 | Quevy et al. |
| 2003/0070917 A1 | 4/2003 | Giaquinta et al. |
| 2005/0269215 A1 | 12/2005 | Horkay et al. |
| 2008/0223719 A1 | 9/2008 | Tam |
| 2010/0066378 A1 | 3/2010 | Ahmadi et al. |
| 2011/0048971 A1 | 3/2011 | Bower et al. |
| 2014/0332410 A1 | 11/2014 | Ben-Yoav et al. |
| 2018/0372667 A1 | 12/2018 | Gupta |
| 2019/0004000 A1 | 1/2019 | Jang et al. |
| 2019/0137425 A1 | 5/2019 | Gupta et al. |

FOREIGN PATENT DOCUMENTS

| | | |
|---|---|---|
| WO | WO-2016/012870 A1 | 1/2016 |
| WO | WO-2017/132564 A2 | 8/2017 |
| WO | WO-2017/132564 A3 | 8/2017 |
| WO | WO-2017/189854 A1 | 11/2017 |
| WO | WO-2018/237348 A1 | 12/2018 |
| WO | WO-2019/221783 A2 | 11/2019 |
| WO | WO-2019/221783 A3 | 11/2019 |

OTHER PUBLICATIONS

International Search Report dated Nov. 20, 2019, for PCT/US2018/061669, filed on Nov. 16, 2018, 4 pages.

Islam, A.B et al. (Dec. 18, 2010). "A Potentiostat Circuit for Multiple Implantable Electrochemical Sensors," Electrical and Computer Engineering (ICECE) 2010 International Conference on, IEEE, Piscataway, NJ USA, pp. 314-317.

Written Opinion dated Nov. 20, 2019, for PCT/US2018/061669, filed on Nov. 16, 2018, 8 pages.

\* cited by examiner

ALL-ELECTRONIC HIGH-THROUGHPUT ANALYTE DETECTION SYSTEM

CROSS-REFERENCE TO RELATED APPLICATIONS

This application is a continuation of U.S. Utility application Ser. No. 16/194,208, filed Nov. 16, 2018 which claims benefit of priority to U.S. Provisional Application No. 62/587,889, filed Nov. 17, 2017, the contents of which is hereby incorporated by reference in its entirety.

STATEMENT AS TO FEDERALLY SPONSORED RESEARCH OR DEVELOPMENT

This invention was made with government support under small business grants DC17PC00018 and DC24PC00024 awarded by the Defense and Advanced Research Projects Agency. The Government has certain rights in the invention.

TECHNICAL FIELD

The subject matter described herein relates to detection of analytes.

BACKGROUND

A potentiostat is commonly used in electrochemical experiments to probe properties of a physical system, for example, an electrochemical interface between a solid and liquid phase. A potentiostat employs a three electrode system that includes a reference electrode, a working electrode and a counter electrode. The potentiostat operates by maintaining a fixed potential difference between a working electrode and a reference electrode and measuring the current that flows through the electrolyte and across the electrode-electrolyte interface either at the counter electrode or at the working electrode. For example, in bulk electrolysis experiments, a potentiostat measures the total charge that has transferred across an electrochemical interface at a fixed potential difference. The measured charge represents the reduction/oxidation reaction at the interface.

The physical system (e.g., electrode-electrolyte interface) probed by the potentiostat includes one or more systems that exhibit quantum properties, e.g., transport properties associated with mesoscale phenomena (phenomena that lie in between the classical and quantum-mechanical regimes of behavior). Traditional potentiostats are limited in their ability to detect quantum properties at room temperature in electrochemical systems. Additionally, traditional potentiostats are unable to selectively detect quantum signatures of the physical system.

Traditional potentiostats are unable to efficiently perform large-scale detection (e.g., detection of multiple quantum properties of an analyte sample, detection of a quantum property of multiple analyte samples, and the like). Large-scale detection may be desirable for achieving desirable accuracy, scalability and throughput. Therefore, it is desirable to develop a detection system that can detect one or more quantum properties of a plurality of physical system (e.g., electrode-electrolyte interface).

SUMMARY

This application provides for an all-electronic detection system that can allow for quick, efficient and accurate detection of analytes in a sample. The detection system has a high throughput (e.g., information delivered per unit time) that can allow for fast and parallelized detection of a broad spectrum of analyte signatures. High-throughput can be achieved by performing multiple detections of one or more analytes in parallel by using an array of sensing modules. For example, a sample can be distributed in the array of sensing modules, and the portion of the sample in each sensing module can be utilized for detection of one or more analytes. Alternately, the array of sensing modules can detect one or more analytes from multiple samples distributed in the array of sensing module. The sensing modules can be designed to allow for improved analyte detection by enhancing analyte transport in the sample. The detection system can be target agnostic, and does not require special sample preparation. For example, unlike various optical detection systems, the detection system is all-electronic and does not require adding reagents to the sample for detection.

The detection system is modular, and can be easily integrated with existing microtiter plate technologies, automated test equipments and lab workflows (e.g., sample handling/distribution systems). For example, the detection system can be integrated with sample storage systems (e.g., microtiter plates, vials, and the like), which can reduce the need for transferring samples and additional processing steps during detection. Furthermore, due to modular design and integration with off-the-shelf component, the detection system is highly scalable.

In one aspect, a sensing module configured to detect an analyte is provided. The sensing module includes a platform configured to couple to a sample well. The sensor also includes a sensor coupled to the platform. The sensing module further includes a first electrode coupled to the platform. The first electrode is configured to electrically connect with the sensor via a feedback circuit. The feedback circuit is configured to provide a feedback signal via the first electrode to a sample received in the sample well, the feedback signal based on a potential of the received sample detected via a second electrode.

In one aspect, the feedback signal is configured to provide excitation control of redox species in the sample at a third electrode located on the sensor. In another aspect, the feedback circuit is configured to detect a current from the sample via the third electrode. The detected current is indicative of an analyte in the sample. In yet another aspect, the first, second and third electrodes are a counter electrode, a reference electrode and a working electrode, respectively, of a potentiostat. In one aspect, the second electrode is co-located on the sensor. In another aspect, the second electrode is mounted on a wall of the sample well (e.g., when integrated with a flexible substrate). In another aspect, the second electrode is located on a cap configured to removably couple to the sample well. The second electrode includes a lead surrounded by a saturated polymeric jacket. In another aspect, the third electrode includes one or more of gold, platinum, copper, silver, and platinum-iridium. In yet another aspect, the platform includes an electromagnetic shield configured to shield the sensor by attenuating external electromagnetic radiation.

In one aspect, one or more of platform and sample well are configured to shield the sample by attenuating external electromagnetic radiation. In another aspect, the first electrode includes a first end and a second end. The first end is coupled to the platform and the second end is configured to electrically connect with the sample in the sample well. In yet another aspect, the second end includes a surface configured to extend across the sample well. The surface and the platform are substantially parallel to each other. In one aspect, the sample well includes a first, a second and a third well electrode configured to electrically connected to the first electrode, the second electrode and the third electrode, respectively. In another aspect, the sample well includes a first end and a second end. The first well electrode is located at the first end of the sample well and the third well electrode is located at the second end of the sample well.

In one aspect, a detection system configured to detect one or more analytes is provided. The detection system includes a platform configured to receive a sample holder that includes a plurality of sample wells. The detection system also includes a plurality of sensing modules coupled to the platform. A sensing module of the plurality of sensing modules includes a sensor coupled to the platform, and a first electrode coupled to the platform. The first electrode is configured to electrically connect with the sensor via a feedback circuit. The feedback circuit is configured to provide a feedback signal via the first electrode to a sample received in a sample well of the plurality of sample wells. The feedback signal is based on a potential of the received sample detected via a second electrode.

In one aspect, the feedback signal is configured to provide excitation control of redox species in the sample at a third electrode in the sensor. In another aspect, the plurality of sample wells are a plurality of vials. In yet another aspect, the sample holder is a microtiter plate.

In one aspect, the detection system includes a readout system that has a plurality of readout channels. A readout channel of the plurality of readout channels includes the feedback circuit. In another aspect, the readout channel includes an analog-to-digital-converter (ADC) configured to digitize one or more of the detected potential of the received sample and the feedback signal. In yet another aspect, the detection system includes a switching matrix configured to electrically connect the readout channel a first sensing module and a second sensing module of the plurality of sensing modules. A first time duration of electrical contact between the readout channel and the first sensing module is temporally separated from a second time duration of electrical contact between the readout channel and the second sensing module. In another aspect, a contact fixture configured to electrically connect the switching matrix with the platform. In another aspect, the readout system is printed on a circuit board.

In one aspect, a method of detecting analytes is described. The method includes detecting a potential associated with a sample received in a sample well by a first electrode. The method also includes generating a feedback signal by a feedback circuit electrically coupled to the first electrode. The method further includes providing the feedback signal to the sample via a second electrode. The feedback signal is configured to provide excitation control of redox species in the sample at a third electrode. The first, the second and the third electrodes are coupled to a platform configured to receive the sample well.

In one aspect, the feedback circuit is configured to detect a current from the sample via the third electrode, the detected current indicative of an analyte in the sample. In another aspect, the first electrode and the third electrode are located on a sensor. In yet another aspect, the platform includes an electromagnetic shield configured to shield the sensor by attenuating external electromagnetic radiation. In one aspect, the first electrode is located on a cap configured to removably couple to the sample well. In another aspect, the first electrode is mounted on a wall of the sample well.

In one aspect, the second electrode includes a first end and a second end. The first end is coupled to the platform and the second end is configured to electrically connect with the sample in the sample well. In another aspect, the second end includes a surface configured to extend across the sample well, the surface and the platform substantially parallel to each other.

DETAILED DESCRIPTION

Figure 1A:
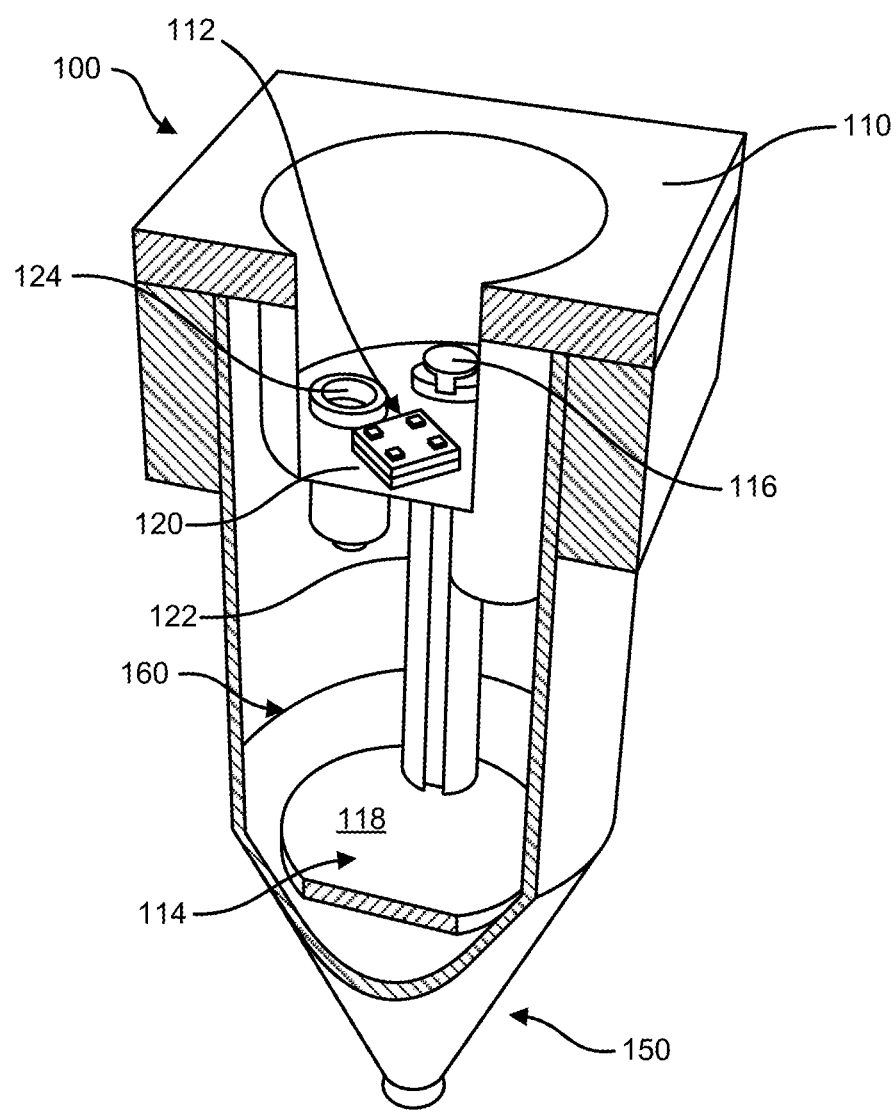
FIG. 1A illustrates a cross section of a sensing module coupled to a sample well.

An all-electronic high-throughput detection system is described. In one implementation, the detection system can include an array of sensing modules that can couple to a sample holder (e.g., microtiter plate, vial rack, and the like). The array of sensing modules can perform multiple analyte detections in parallel (e.g., simultaneously). A sensing module can couple to a sample well (e.g., a well from the microtiter plate, a vial, and the like) which can hold a sample. The sample can include, for example, redox species and analyte samples. The sensing module can include a vibronic sensor that can establish electrical contact with the sample in the sample well. Once an electrical contact has been established, the vibronic senor can detect one or more analytes in the sample.

The array of sensing modules can make multiple detections in parallel. For example, the detection system can detect analytes in multiple samples (e.g., the multiple samples placed in multiple sample wells). This results in a higher through-put compared to a system that performs detection on one sample at a time. Multiple detection in parallel can also improve the accuracy of analyte detection. For example, a sample can be distributed over multiple sample wells (e.g., multiple vials, multiple wells of a microtiter plate) and detected by multiple sensing modules in the array. This can enable quick and large-scale data collection that can provide statistically large population of data for accurate detection. Accurate detection may be desirable, for example, in the development of complex panel assays for food safety or clinical applications.

The vibronic sensor of a sensing module can be a potentiostat with a high-gain low-noise feedback system as described in Provisional Application No. 62/328,798 and PCT Application Serial No. PCT/US2017/29854, the contents of which are incorporated herein by reference in its entirety. Other vibronic sensor architectures have been described in U.S. Pat. No. 9,285,336, U.S. application Ser. No. 14/455,205, and Provisional Application No. 62/523,729 and U.S. application Ser. No. 16/016,468, which are incorporated herein by reference in their entirety.

The vibronic sensor can include electrodes (e.g., reference electrodes, counter electrodes and working electrodes) and a high-gain low-noise feedback circuit. The vibronic sensor can detect electrical properties of the sample (e.g., potential) via the reference electrode, and the feedback circuit can provide a feedback signal (e.g., feedback current) via the counter electrode. The feedback signal can suppress dissipative effects of thermodynamic environment on the interaction between analytes and vibronic states of redox species in the sample. This can allow for room temperature detection of signatures of analytes (e.g., analyte depenent currents) at the working electrode.

The vibronic sensor can be modular that makes it compact and easily integrable with the existing devices and measurement techniques. For example, the reference electrode, counter electrodes, working electrodes and the feedback circuit can form separate modules which can be electrically connected to form the vibronic sensor. In some implementations, parts of the vibronic sensors can be coupled to a sample well (e.g., microtiter well, vial, and the like) designed to hold the sample. In some implementations, the reference and working electrodes can be coupled together to form a chip scale sensor. In other implementations, the chip scale sensor only includes the working electrode. The chip scale sensor can be designed to couple/decouple with a holder in the sensing module by a mechanical clip, low temperature adhesive, UV curable adhesive, and the like. The sensing module can include an electromagnetic shield to protect the portions of the vibronic sensor (e.g., chip scale sensor, counter electrode, working electrode, reference electrode, and the like). The electromagnetic shield can include, for example, a metallic cage-like structure that can surround portions of the vibronic sensor and attenuate ambient electromagnetic radiation (e.g., radiation emanating from readout circuitry and the ambient surrounding).

The modular vibronic sensor design can have a separate counter electrode with a geometry and an orientation that allows for fast and accurate detection of analytes. For example, it can be designed to have a large contact area with the sample. A portion of the counter electrode can be a flat surface that can be immersed in the sample. The large contact area can increase the flux of charge carrying redox species from the counter electrode to the working electrode (e.g., located on the chip scale sensor) and vice-versa. The flux of redox species can drive species in the sample (e.g., analytes, redox species) towards the working electrode in the chip scale sensor. This can improve the accuracy of analyte signature detection at the working electrode (e.g., by resulting in a stronger detection signal). The flux of redox species can also be varied by varying the distance between the counter electrode and the working electrode.

In some implementations, feedback circuits associated with the various sensing modules can be included in a readout system. The readout system can be implemented, for example, as a printed circuit board. Details of a readout circuit in the readout system is described in Provisional Application No. 62/328,798 and PCT Application Serial No. PCT/US2017/29854, which are incorporated herein by reference in its entirety. The readout system can include multiple readout channels. A readout channel can include sensing and feedback circuitry of the sensing modules. The readout channel can detect potential of a sample in the sample well via the reference electrode, and based on the detected potential provide a feedback signal (e.g., current signal) via the counter electrode. The readout channel can detect a current signal from the working electrode that can contain signatures of analytes in the sample. Furthermore, the readout channel can digitize the data of detected sample properties (e.g., by an analog-to-digital converter [ADC]), and can provide the digitized data to an external computing device.

In one implementation, the readout system can be integrated with the detection system. For example, readout channel can be fabricated as an application specific integrated circuit. In other implementations the readout system can be included in a handheld device that can be electrically connected to the detection system (e.g., at the time of detection). The readout system can communicate with a computing device, either wirelessly or via a serial bus connection. For example, a readout channel integrated/fabricated with the chip scale sensor can wirelessly transmit information related to sample detection, feedback system, and the like. This can make the sensing module that includes the aforementioned chip scale sensor an independent detection system capable of detecting analytes.

The readout system can be electrically connected to the sensing modules of the detection system via a contact fixture. The contact fixture can include conductive pins that are spatially distributed to contact the sensing modules (e.g., vibronic sensor in the sensing module). The spatial distribution of the conductive pins can be based on a predetermined geometry of the sensing modules (e.g., spatial location of working electrode, reference electrode and reference electrode in the vibronic sensor module).

In conjunction with the contact fixture, the electrical connection between the readout system and the sensing module can be established by a switching matrix. The switching matrix can allow a readout channel in the readout system to control the operation (e.g., provide feedback signal, detect sample potential, and the like) of multiple sensing modules. The switching matrix can establish a time-sharing scheme where the readout channel sequentially controls multiple sensing modules. In one implementation, the switching matrix can designate a predetermined operation time during which a read out channel interacts with a sensing module. After the predetermined operation time has elapsed, the read out channel interacts with another sensing module. The switching matrix can be programmed to dynamically change the operation time. For example, the switching matrix can allow for a longer operation time for samples with anaytes that take longer to detect. Alternately, if the threshold accuracy of detection changes, the operation time can accordingly change (e.g., longer operation time for greater accuracy).

One or more samples can be deposited in the sample storage (e.g., wells of a microtiter plate, vials in a vial rack) by a liquid handler. The liquid handler can determine the volume of sample to be deposited in a sample well of the sample storage. For example, in some implementations the volume of sample in a sample well should be greater than a threshold value in order to establish electrical connection between vibronic sensing module (e.g., working electrode, reference electrode, counter electrode, and the like) and the sample. In some implementations, the liquid handler can track the sample delivery process (e.g., properties of samples deposited in the sample storage, time of delivery, sample volume, and the like). The liquid handler can also identify the sample storage. For example, the liquid handler can include a camera (e.g., attached to a sensing system in FIG. 11) that can identify an identifier (e.g., QR code, barcode, etc.) associated with the sample storage. The liquid handler can include robotic interfaces that can pipette liquid into the sample storage and can be distinct from the integrated socket.

The volume ratio of redox species and analyte sample has a desired predetermined value that can be maintained by the liquid handling procedures or apparatus. For example, the liquid handler can add a volume of analyte sample in the sample well followed by a volume of redox species (or vice versa). The ratio of the volumes can be selected to prevent undersired reactions at the chip-scale sensor-sample interface (e.g., prevent/reduce excessive accumulation of species at the working electrode that adversely affect the detection process). In one implementation, the volume of the electrolyte containing the redox species can range from about 0.5 milliliter (mL) to about 1 mL, and the volume of the sample can range from about 1 microliter to 100 microliter.

Implementations of Analyte Detection System.

FIG. 1A illustrates a cross section of a sensing module 100 coupled to a microtiter well 150 (a sample well). The sensing module 100 includes a platform 110 that can couple to a chip scale sensor 112 and an electrode 114. For example, the platform 110 can include holders 120 and 122 that are designed to receive/mate with chip scale sensor 112 and electrode 114 respectively. The holders 120 and 122 can include an electromagnetic shield to protect the chip scale sensor 112 and electrode 114 from external electromagnetic radiation. The platform 110 can also couple with the microtiter well 150 to enclose a volume 160 that can hold a sample (e.g., electrochemical solution with redox species and analytes). The sample can be introduced into the volume 160 through the inlet 124 in the platform 110. Alternately or additionally, sample can be placed in the microtiter well before the platform 110 is coupled to the microtiter well 150.

A first end 116 of the electrode 114 is coupled to the platform 110 via the holder 122. A second end 118 of the electrode 114 can extend across a portion of the volume 160. For example, the second end 118 can be a flat surface that extends parallel to the platform 110. Large surface area of the second end 118 can establish a robust and/or uniform electrical connection between the first electrode and the sample in volume 160.

The chip scale sensor 112 and electrode 114 are configured to make contact with the sample in the volume 160. For example, platform 110 can include an orifice where the chip scale sensor is received. A surface of the chip scale sensor 112 proximal to the platform 110 can contact the sample in the volume 160 through the orifice. The proximal surface of the chip scale sensor 112 can include multiple electrodes (e.g., working electrode, reference electrode, and the like) that can contact the sample. The second end 118 of the electrode 114 can also contact the sample in the volume 160. For example, the second end 118 can be submerged in the sample contained in the volume 160.

The chip scale sensor 112 and the electrode 114 can be electrically connected, for example, via a feedback circuit (e.g., feedback circuit in a readout channel) and/or the sample in the microtiter well 150. The chip scale sensor can include conductive pins that can establish electrical contact with the feedback circuit (e.g., feedback circuit in the readout channel). The conductive pins can be located on a distal surface of the chip scale sensor which is located on the opposite side of the proximal surface of the chip scale sensor. The first end 116 of the electrode 114 can be in electrical contact with the feedback system. The chip scale sensor 112 and the electrode 114 can be connected to a contact fixture (e.g., contact fixture described above). As described later, in some implementations, the chip scale sensor 112 and the first electrode can be electrically connected to a readout circuit (e.g., located in the readout channel) that can include the sensing and feedback systems, via a switiching matrix.

The electrodes on the chip scale sensor 112, the first electrode 114 and the feedback system can constitute a potentiostatic apparatus that can detect one or more analyte through detection of mesoscale/quantum properties as described in Provisional Application No. 62/328,798 and PCT Application Serial No. PCT/US2017/29854, which are incorporated herein by reference in its entirety. The potentiostatic apparatus (also referred to as "vibronic sensor" or "vibronic sensor module") can detect analytes in a sample by detecting the effect of analytes on vibronic states of redox species in the sample during an electron transition process.

The first electrode 114 can act as a counter electrode of the vibronic sensor, and a second and third electrode on the proximal surface of the chip scale sensor 112 can act as the reference electrode and working electrode, respectively, of the vibronic sensor. The feedback system can have low-noise (e.g., based on cascaded high-gain amplifier design), and can detect a potential associated with the sample in the volume 160 via the reference electrode in chip scale sensor 112. Based on the detected potential, the feedback system can provide a feedback signal (e.g., feedback current) to the sample via the first electrode.

The redox species in the sample can exchange electrons at the counter electrode and the working electrode (e.g., gain/lose one or more electrons). Analytes located in proximity to the working electrode can affect the electron exchange process at the working electrode by perturbing the vibronic states of the redox species. As a result, the current generated by the exchange of electrons at the working electrode can include signatures of the analytes. Analytes can be determined by detecting the current at the working electrode, and analyzing the detected current (e.g., by comparing the detected current with analyte characteristic information in a database).

Properties of the working electrode can be determined based on various design consideration that is discussed in detail in Provisional Application No. 62/523,729 and U.S. application Ser. No. 16/016,468, which are incorporated herein by reference in their entirety. The working electrode can include a nano-scale electrochemical interface that can allow for selective detection of quantum signatures in a charge transfer processes at the electrochemical interface.

Figure 1B:
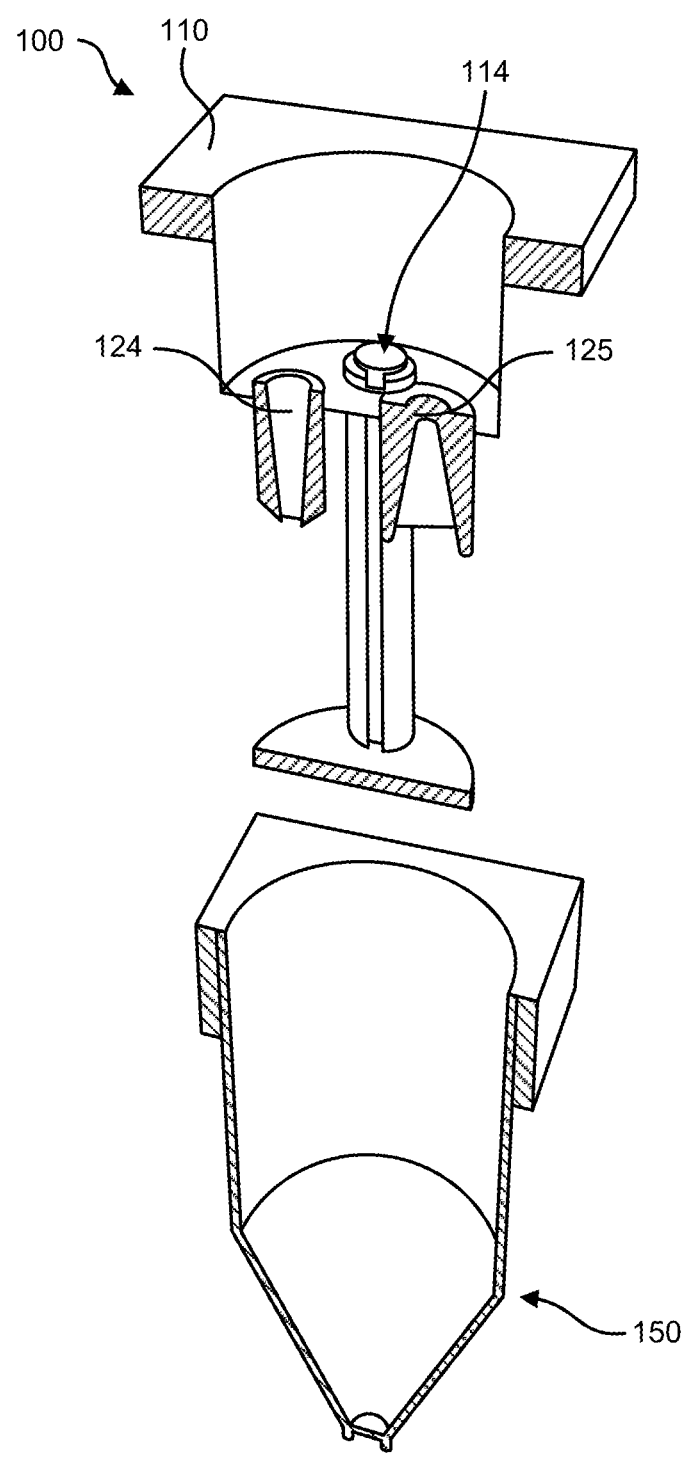
FIG. 1B illustrates an exploded view of FIG. 1A.
Figure 1C:
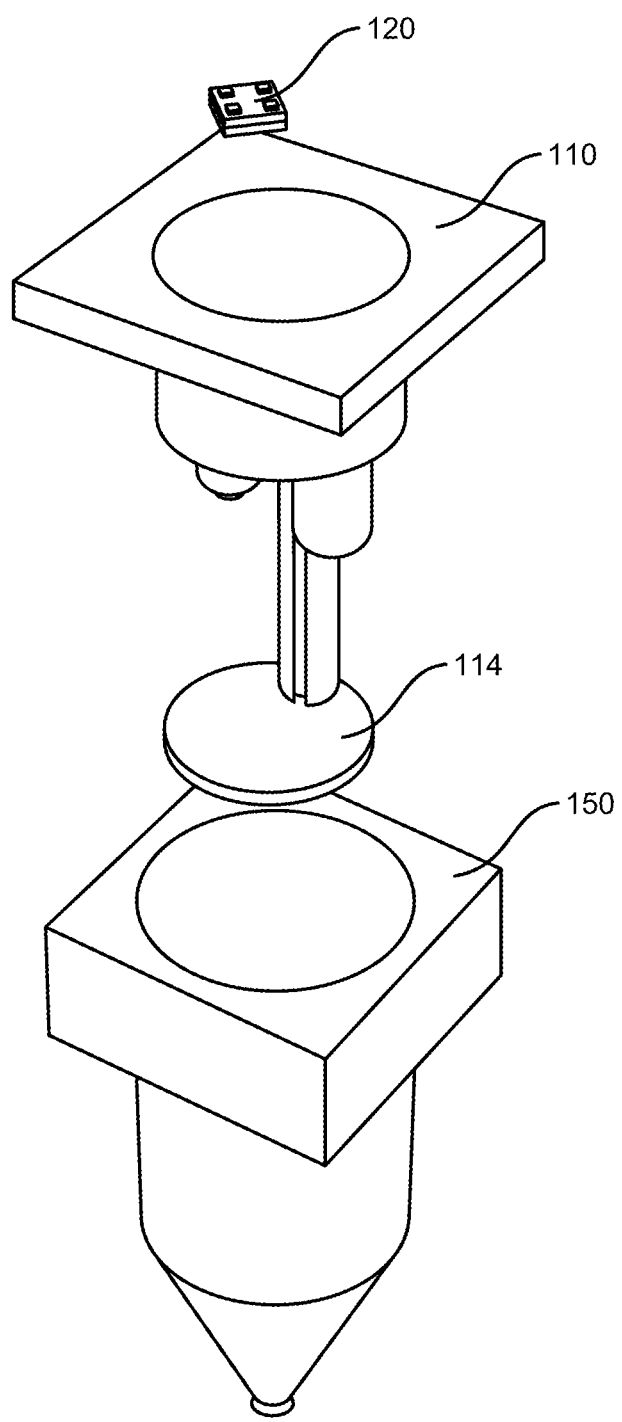
FIG. 1C illustrates an exploded perspective view of FIG. 1A.

FIG. 1B illustrates a cross section of an exploded view of the sensing module 100 and sample well 150 in FIG. 1A. After a sample with analytes is deposited in the sample well 150 (e.g., by the liquid handler), the the sensing module 100 can be suspended into the sample well 150 such that the distal end of the counter electrode 114 is in electrical contact with the sample. In other implementations, the sample can be introduced in the sample well via an inlet (e.g., inlet 124, 125) in the platform 110. If the volume of the sample exceeds the volume of sample well 150, the excess sample/ trapped bubbles can flow out of the inlets 124, 125. The inlets 124, 125 can have microfluidic features to induce transport of sample species in the sample well 150 using surface tension and capillary effects. FIG. 1C illustrates an exploded perspective view of the sensing module in FIG. 1A.

Figure 2:
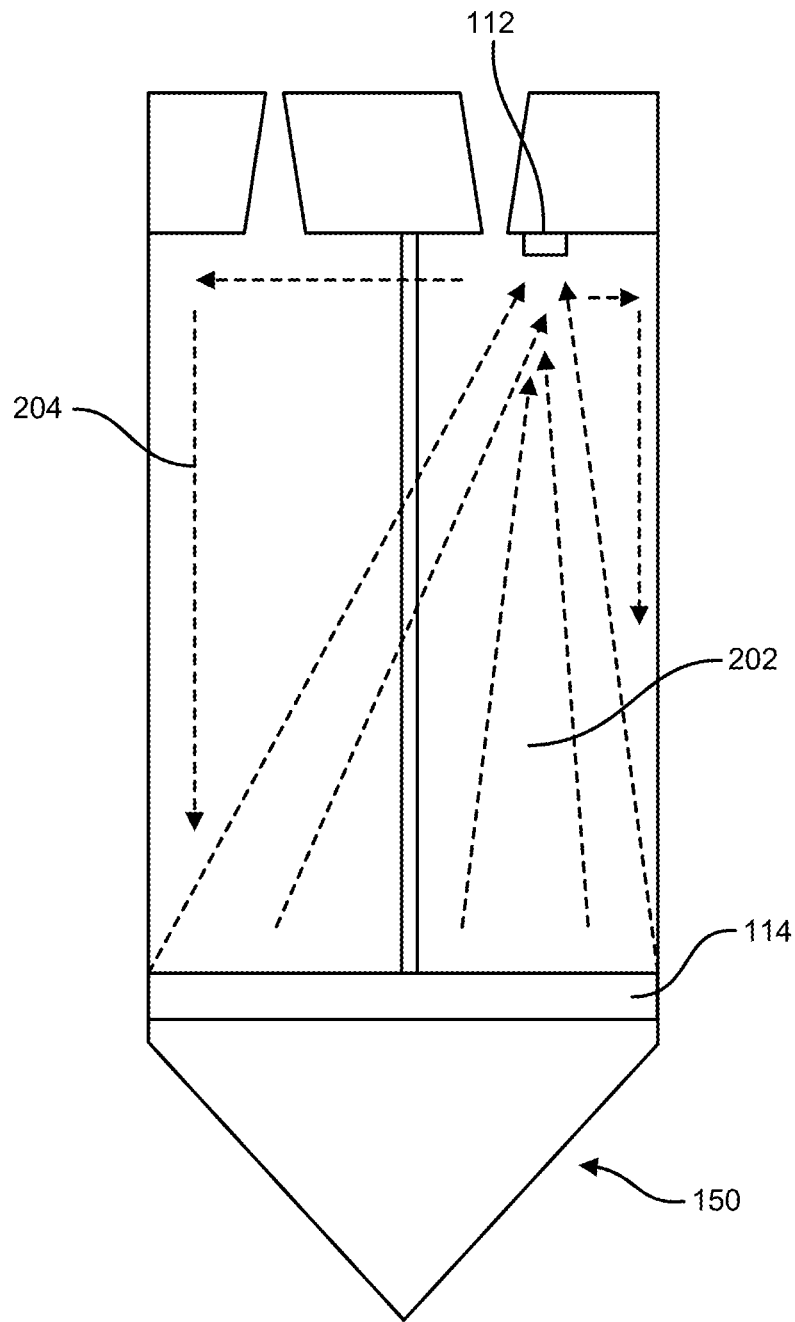
FIG. 2 illustrates a schematic rendering of transport of species in the sample well-sensing module system of FIG. 1A.

FIG. 2 illustrates a schematic rendering of transport of species in the sample well-sensing module system of FIG. 1A. The sample well 150 is designed to facilitate robust electrical contact between vibronic sensor (e.g., chip scale sensor 112, counter electrode 114) and the enclosed sample. For example, volume of the the sample ("sample volume") can be determined such that when added in the sample well 150, chip scale sensor 112 and counter electrode 114 establish electrical contact with the sample. The location and size of the counter electrode 114 can determine the rate of transport of species in the sample (e.g., redox species, analytes, and the like) between the counter electrode 114 and the chip scale sensor 112. For example, the distance between the counter electrode 114 and the chip scale sensor 112 can determine a transport zone 202 of the recirculating flow of the redox species due to the oxidation-redution reactions occurring at the working electrode (located in the chip scale sensor 112) and counter electrode 114 (also referred to as "transport cone"). The transport of the sample can occur in the transport zone 202. After a volume of sample reaches the chip scale sensor 112, it can recirculate back towards the counter electrode 114 (e.g., along a sample flow channel 204). The electrochemical potential gradient set up between the counter and working electrodes can determine the nature of the flux of species in the sample well volume. As the electrochemical potential gradient/flux of the species increases, the travel time of the specie between the counter electrode 114 and the chip scale sensor 112 can decrease. This can decrease the time needed for detecting the sample.

The counter electrode 114 can be much larger than the chip scale sensor 112 to ensure that the flux of the redox species covers the entire cross-sectional area of the sample volume. The redox specie can drag the analyte as it moves from the counter electrode 114 to the chip scale sensor 112. Because the detection of analytes occurs at the chip scale sensor 112, it can be desirable to increase the flux of the redox species. It can also be desirable to increase the volume of the transport zone so that more analytes are dragged by the diffusion of the redox species (e.g., by viscous forces from the solvent). The volume of the transport zone 202 can be increased by increasing the distance between the chip scale sensor 112 and the counter electrode 114 and/or the size of the counter electrode 114.

Figure 3A:
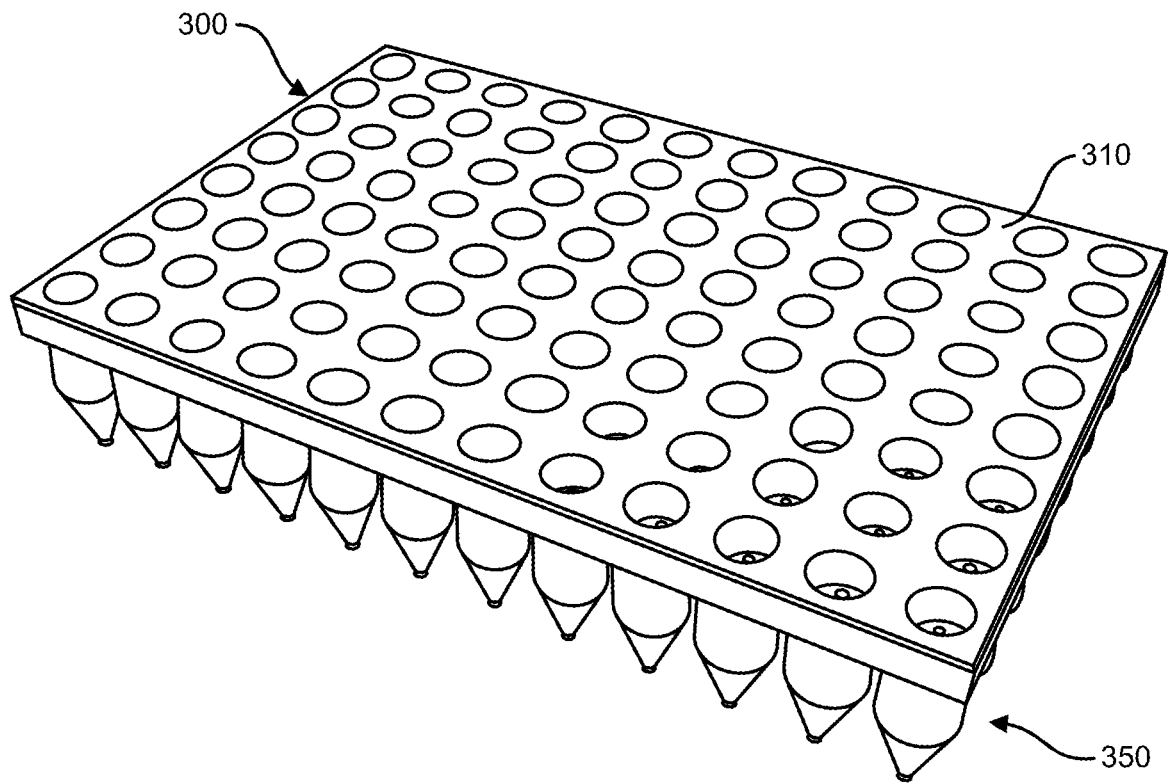
FIG. 3A illustrates a perspective view of a sensor array coupled to a microtiter plate.

FIG. 3A illustrates a perspective view of a detection system 300 that includes an array of sensing modules attached to a platform 310. The detection system 300 can couple with a microtiter plate 350. For example, the sensing modules of the detection system 300 can couple with the wells of the microtiter plate 350. The various sensing modules can perform analyte detection of multiple samples in the microtiter plate 350 in parallel (e.g., simultaneously).

Figure 3B:
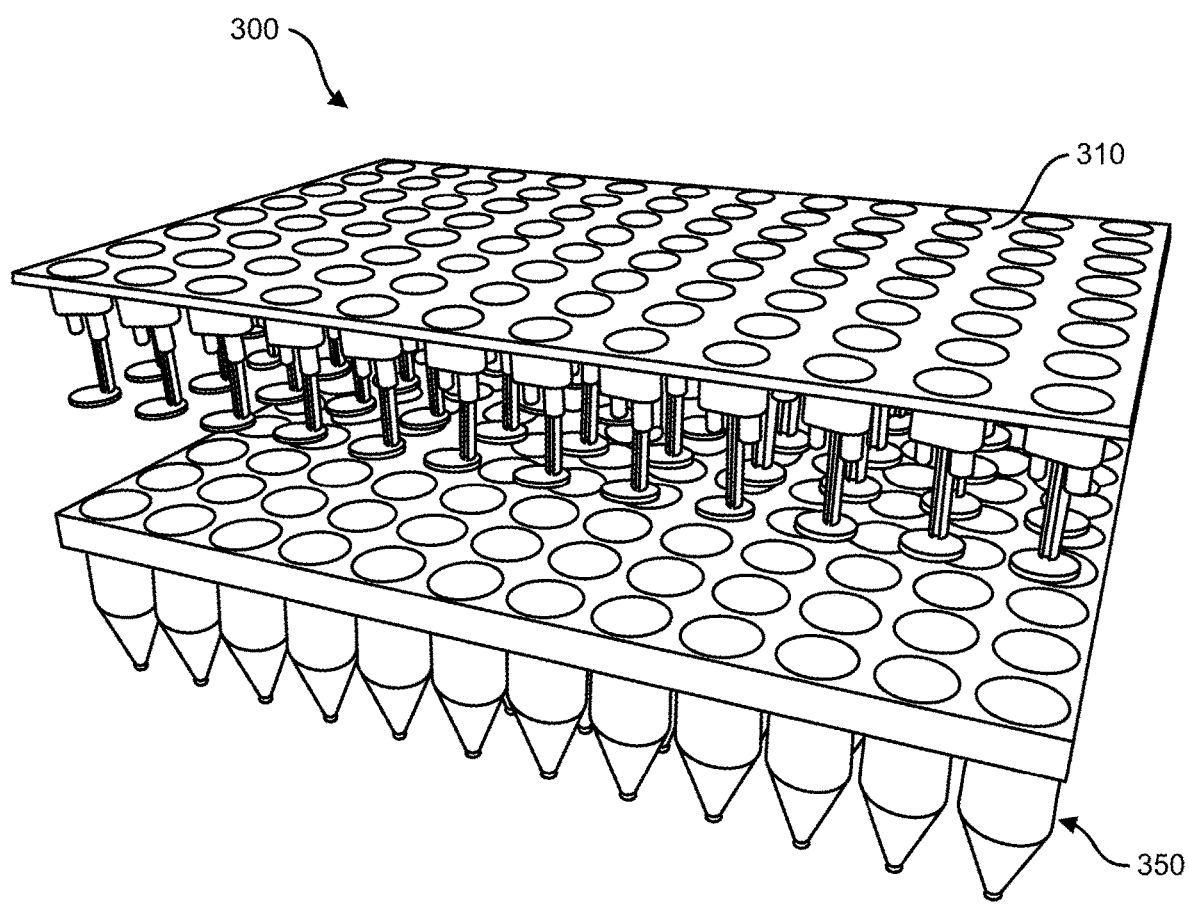
FIG. 3B illustrates an exploded view of the sensor array and microtiter plate illustrated in FIG. 3A.

FIG. 3B illustrates an exploded view of the sensor array and microtiter plate illustrated in FIG. 3A.

Figure 4:
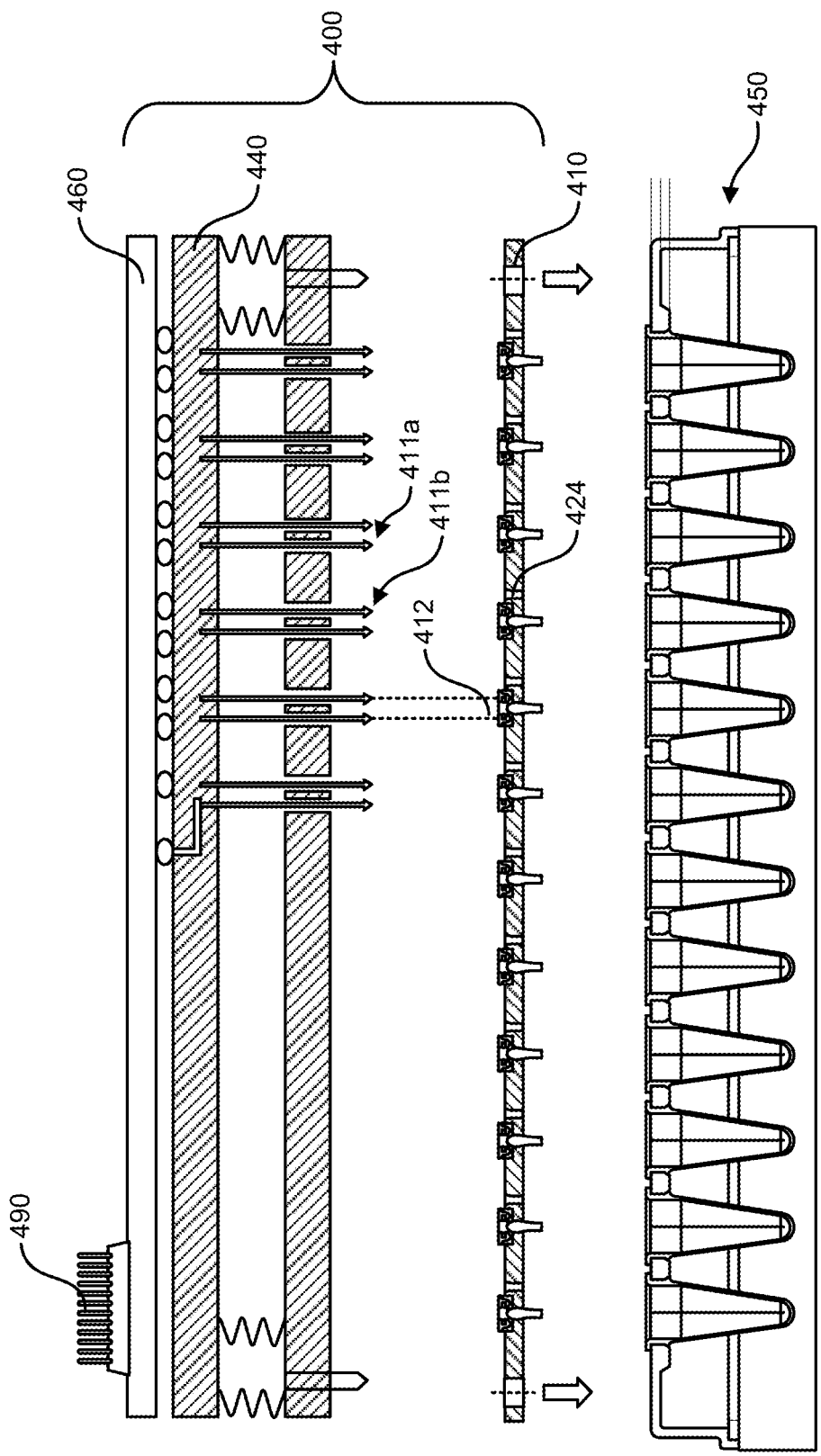
FIG. 4 illustrates a schematic view of a detection system.

FIG. 4 illustrates a schematic view of an implementation of a detection system 400 that can detect analytes in samples placed in the wells of the microtitier plate 450. The image of the detection system 400 has been exploded to illustrate the platform 410, the contact fixture 440 and an interface board 460. The platform 410 can include multiple sensing modules. A sensing module can include chip scale sensor 412 and inlets 424. The contact fixture 440 can be electrically connected to the platform 410 by multiple testing probes/ conducting pins 411*a,b*. The conducting pins can be geometrically arranged to make electrical contact with the chip scale sensors 412 (e.g., working electrode and reference electrode in the chip scale sensor) and counter electrodes (not shown). The contact fixture 440 can be in electrical contact with the interface board 460. The interface board 460 can include the readout system. The contact fixture 440 can establish electrical connection between the readout channels of the readout system and sensing modules of the detection system 400. After an electrical contact has been established between a readout channel (which includes sensing and feedback circuits) and a sensing module (e.g., counter electrode, working electrode, reference electrode of the sensing module), detection of analytes in the microtiter plate 450 can be performed.

In some implementations, the detection system 400 can include a switching matrix. The switching matrix can be incorporated in the interface board 460, contact fixture 440 or can be included in a separate module. The switching matrix can serve as an interface between the interface board 460 and the contact fixture 440. As described before, the switching matrix can be establish electrical connection between a readout channel and multiple sensing modules (e.g., sequentially in time). For example, eight readout channels can drive eight sensing modules in parallel. If the detection system includes ninety six sensing modules (e.g., for a microtiter plate having ninety six wells), and eight sensing modules can be driven in parallel, the detection system can perform analyte detection in all ninety six sensing modules in twelve steps. If the expected time of detection of each step is 10 minutes, the total detection time will be about two hours.

The interface board 460 also includes pins 490 through which communication with an external computing device can be established. In some implementations, the interface board 460 can wirelessly communicate with an external device (e.g., by short-range wireless communication methods like WiFi, Bluetooth, and the like.). The interface board 460 can digitize sensing/feedback information of the various sensing modules and upload the information to a database in the computing device.

Figure 5:
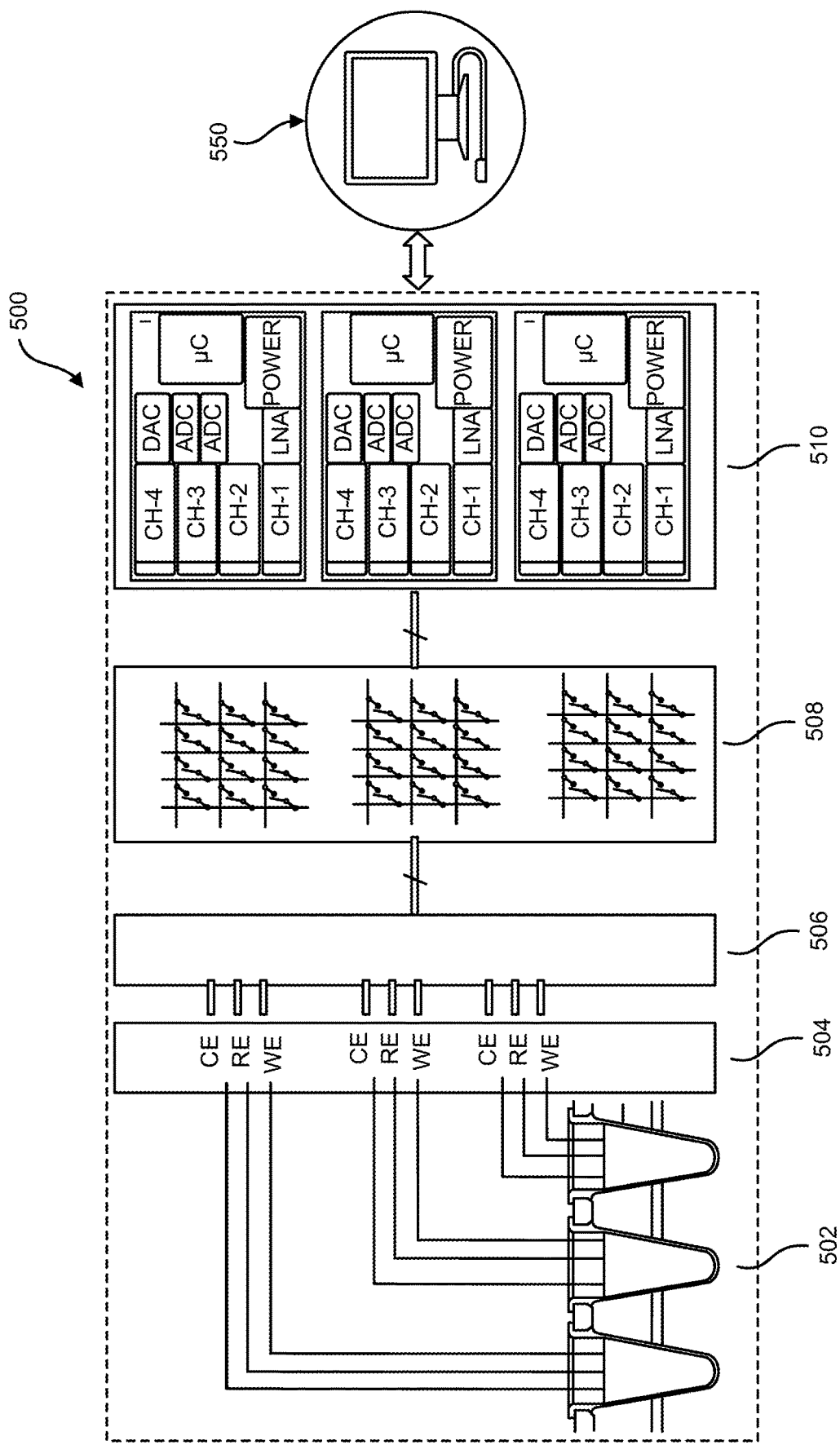
FIG. 5 illustrates a schematic view of a detection system in communication with a computing device.

FIG. 5 illustrates a schematic view of a detection system 500 in communication with a computing device 550 as described above. The detection system 500 can include a plurality of microtiter plates 502 (e.g., microtitier plate 450), a platform 504 (e.g., platform 410), a contact fixture 506 (e.g., contact fixture 440), a switching matrix 508 and a readout system 510.

In some implementations, the interface board 460, contact fixture 440 and switching matrix can be integrated to form a testing module. A testing module can be designed for a known detection system, and can be available off-the shelf. During detection, a user can assemble the testing module with the corresponding detection system. Such a configuration improves the modularity of high-throughput analyte detection process.

Figure 6:
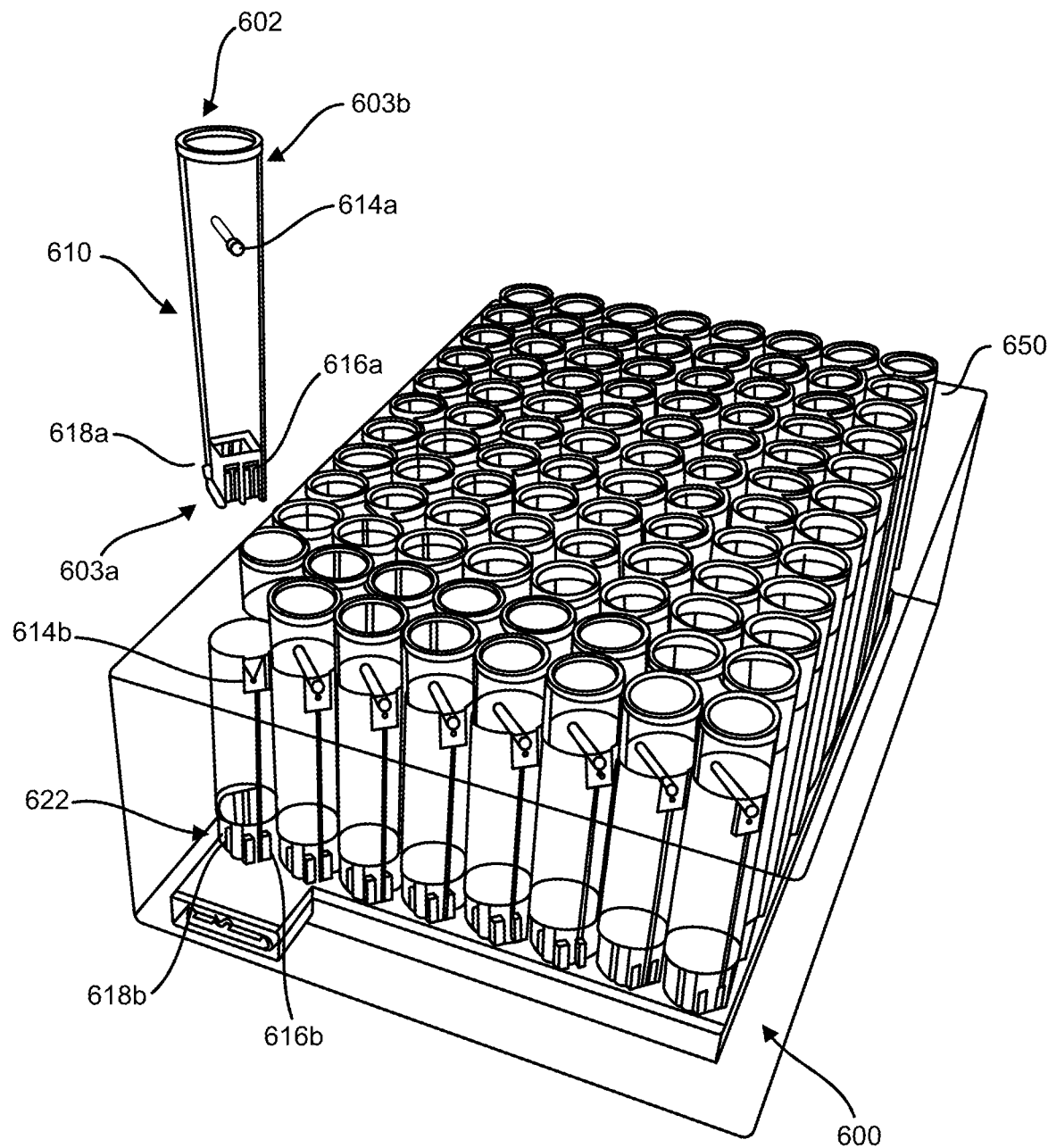
FIG. 6 illustrates an implementation of a detection system.

FIGS. 6-10 illustrate another implementation of an analyte detection system. FIG. 6 illustrates a detection system 600 that can receive multiple vials in a vial rack 650. A vial 602 can include a vial well 610 that receive a sample for analyte detection. The inner wall of the vial well 610 can include/couple to multiple electrodes that can electrically contact the sample in the vial well 610. The vial 602 can include a base module 620 (see FIG. 7A) located at the base of the vial well 610. The base module 620 can be monolithically fabricated with the vial well 610 (e.g., by moulding) at a distal end 603a. The vial well 610 can include a first electrode 614a (e.g., located at a proximal end 603b of the vial 602). The base module 620 can include a second electrode 616a. The vial well 610 can include a third electrode 618a. The first, second and third electrodes can extend to the outer surface of the vial 602 and can electrically couple to external electrodes/power connections. (e.g., second electrode 616a can be electrically connected to a flex connector 630 located on the base module 620). The vial 602 can be coupled with a sensing module 622 of the detection system 600. When the vial 602 is coupled with the sensing module 622 (e.g., when the vial is directed into the vial rack 650), portions of the vial electrodes can come in electrical contact with electrodes of the sensing module 622. For example, counter electrode 614b of the sensing module 622 can establish electrical contact with the first electrode 614a of the vial 602, reference electrode 618b of the sensing module 622 can establish electrical contact with the third electrode 618a of the vial 602, and working electrode 616b of the sensing module 622 can establish electrical contact with the second electrode 616a of the vial 602. After an electrical contact has been established between the electrodes of the the vial and the electrodes of the sensing module 622 (e.g., 614b, 616b and 618b), electrodes 614a, 616a and 618a can operate as counter, working and reference electrodes, respectively. The sensing module 622 can include a low-noise feedback system (e.g., low-noise feedback system described in Provisional Application No. 62/328,798) that can electrically couple to the counter electrode 614b, working electrode 616b and reference electrode 618b. The low-noise feedback system can detect analytes in the sample received by the vial well 610.

In some implementations, electrode 618a can be replaced by an electrode system (not shown) mounted on the inner wall of the vial 602. The electrode system can can include an electrode (e.g., a screen printed Ag/AgCl/KCl polymer jacketed electrode) integrated on a flex and mounted on the inner wall 602. The electrode system can conform to the shape of the the inner wall of the vial 602. For example, the electrode system can have a shape of a sheet that can couple to the inner wall of the vial 602.

Figure 7A:
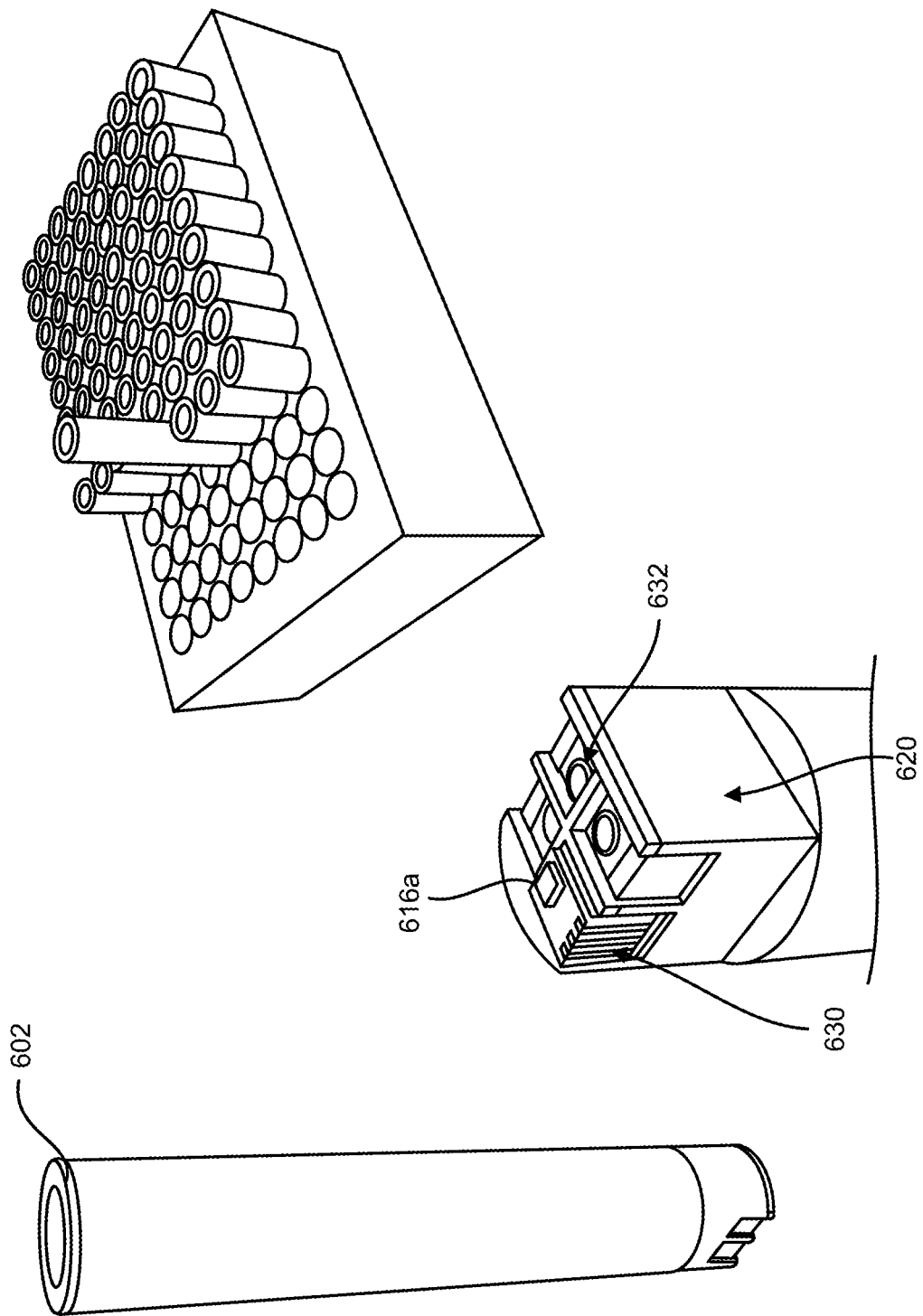
FIG. 7A illustrates coupling between a vial and a sensing module of the detection system in FIG. 6.

FIG. 7A illustrates the base module 620 of the vial 602. The detection system 600 can includes multiple sensing modules (e.g., array of sensing modules). The vial 602 can be coupled (e.g., mechanically attached) with the sensing module 622. For example, an attachment mechanism such as a clip or a socket can engage the vial 602 with the sensing module 622 when the latter is pushed against the sensing module 622. The base module 620 can include access port 632 that can, for example, allow the sample in the vial 602 to contact the working electrode. The flex connectors 630 can be designed to mate with electrode 616b of the sensing module 622.

Figure 7B:
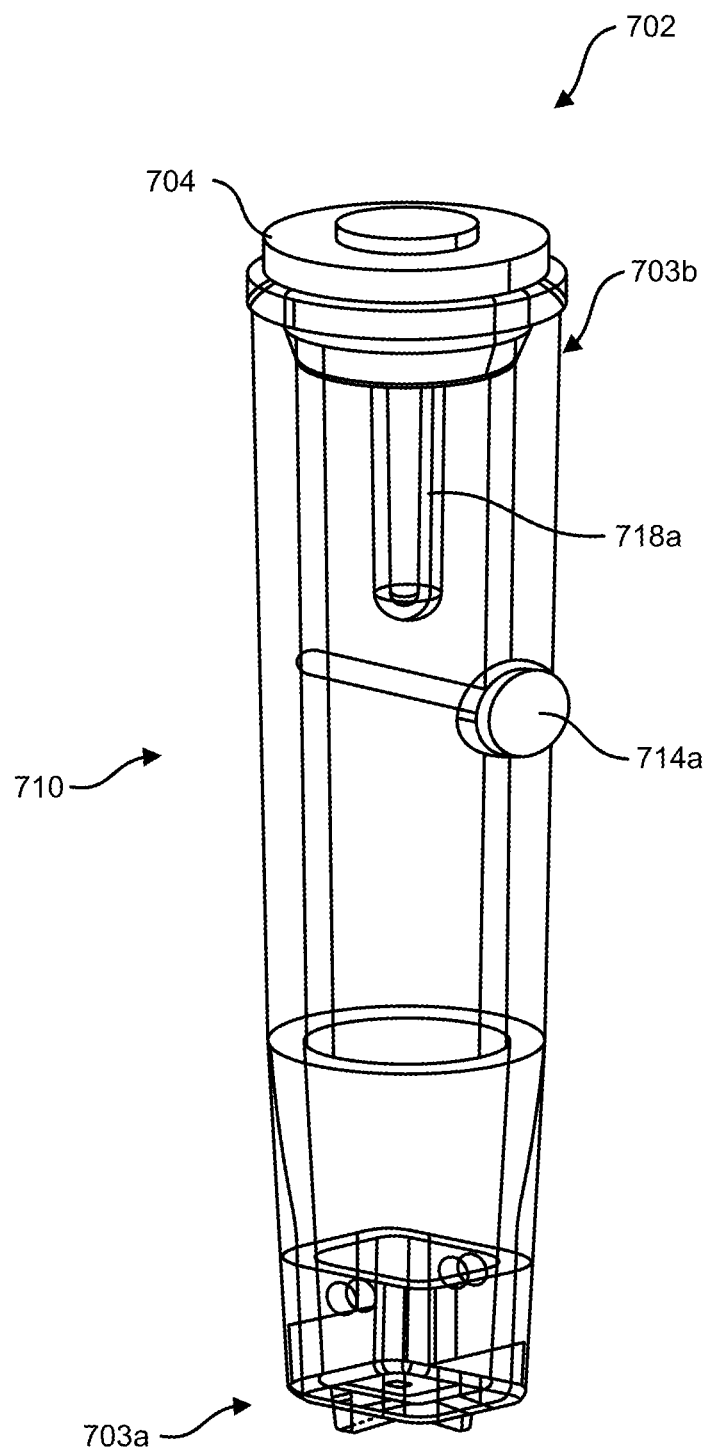
FIG. 7B illustrates another exemplary implementation of a vial.

FIG. 7B illustrates another exemplary implementation of a vial. The vial 702 includes a cap 704 that can removably couple to a vial well 710. The vial well 710 can receive a sample for analyte detection. The inner wall of the vial well 710 can include/couple to a first electrode 714a, and the cap 704 can include/couple to a second electrode 718a. For example, the first and second electrodes 714a and 718a can be located at a proximal end 703b of the vial 702. The first electrode 714a and the second electrode 718b can electrically couple with the sample in the vial well 710. The vial 702 can include a base module (not shown) at a distal end 703a of the vial 702. The vial well 710 can include a third electrode (not shown) at the distal end 703a of the vial 702.

The vial 702 can be coupled with a sensing module of a detection system. When the vial 702 is coupled with the sensing module, portions of the first electrode 714a, second electrode 718a and the third electrode of the vial 702 can come in electrical contact with electrodes of the sensing module. For example, the first electrode 714a, the second electrode 718a and the third electrode can couple to couple to a counter electrode, a reference electrode and a working electrode, respectively, of the sensing module. After an electrical contact has been established between the electrodes of the the vial 702 and the electrodes of the sensing module, electrodes 714a, and 718a can operate as counter, and reference electrodes, respectively. The third electrode can operate as a working electrode.

Figure 7C:
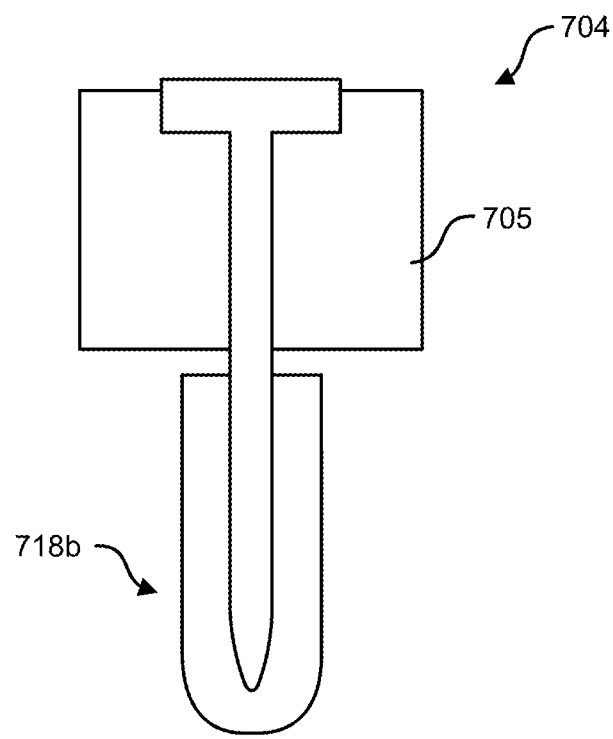
FIG. 7C is a schematic illustration of a cap configured to removably couple with the vial in FIG. 7B.
Figure 7D:
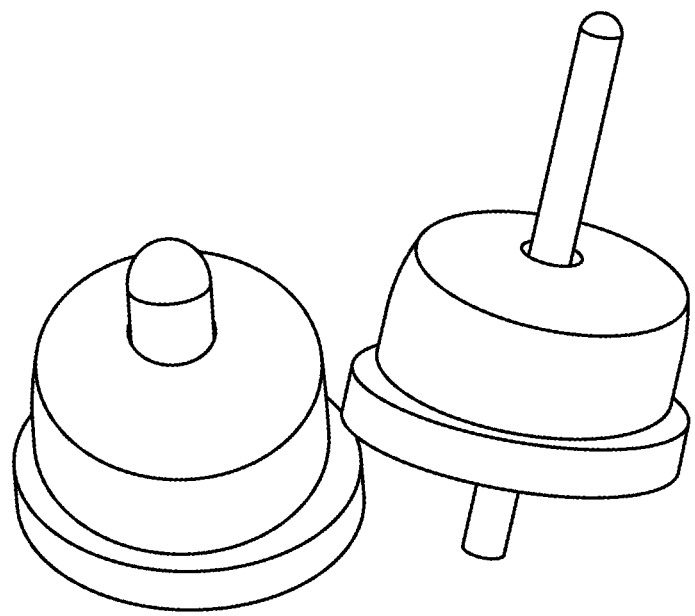
FIG. 7D illustrates a perspective view of exemplary implementations of the cap in FIG. 7C.

FIG. 7C is a schematic illustration of the cap 704. The cap 704 includes a base 705 that can mechanically couple with the vial well 710 (e.g., at distal end 703b of the vial well 710). The cap 704 can also include the second electrode 718b that can establish electrical contact with the sample in the vial well 710. In some implementations, the second electrode 718b can include of a pin assembly (e.g., composite heterogeneous pin assembly made of one or more of Ag plating, AgCl, 3M halogenated salt like KCl, NaCl, etc.) surrounded by a saturated polymeric jacket. The pin assembly can be integrated into the base 705. FIG. 7D illustrates a perspective view of exemplary implementations of the cap 704.

Figure 8:
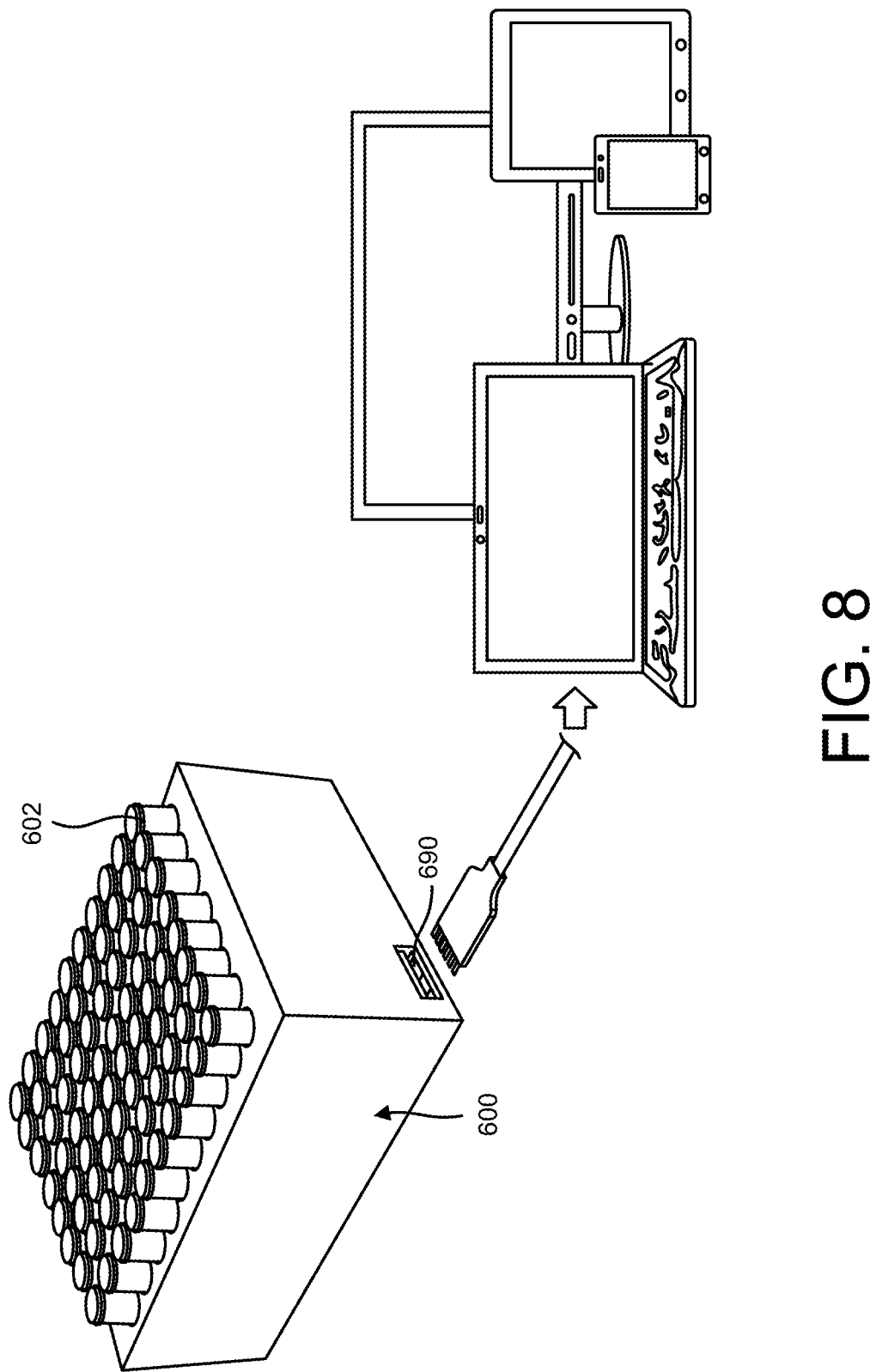
FIG. 8 illustrates the detection system of FIG. 6 configured to communicate with an external computing device.

The detector 600 can include the contact fixture, the switching matrix and the readout system. For example, they can be located below the array of sensing modules. As illustrated in FIG. 8, the detection system 600 can communicate with an external computing device via serial bus 690 or via short-range wireless communication. The sensing module 620 can act as an independent detection system that can detect an analyte and transfer sensing/feedback information to the external computing device.

Method of Use

In one implementation, a sample can be placed in one or more sample wells (e.g., microtiter well, vial, and the like) of an analyte detection system including an array of sensing modules (e.g., detection system 400, 600 and the like). The sample includes analyte samples and electrolyte (having redox species). Analyte samples (e.g., blood) include the analytes to be detected (e.g., DNA, RNA oligomers, peptide fragments, proteins, glycans, polysaccharides, metabolites, pathogenic organisms and the like). The electrolyte (e.g., an aqueous solvent, an organic solvent, and the like) can include redox species (e.g., ferro-/ferricyanide couple, ferrocenium ion and ruthenium hexaamine complex, potassium hexacyanoferrate (ii)/(iii), and the like). In exemplary samples, the concentration of analyte in the sample can range from 1 pg/ml to 1 mg/dl.

Figure 9:
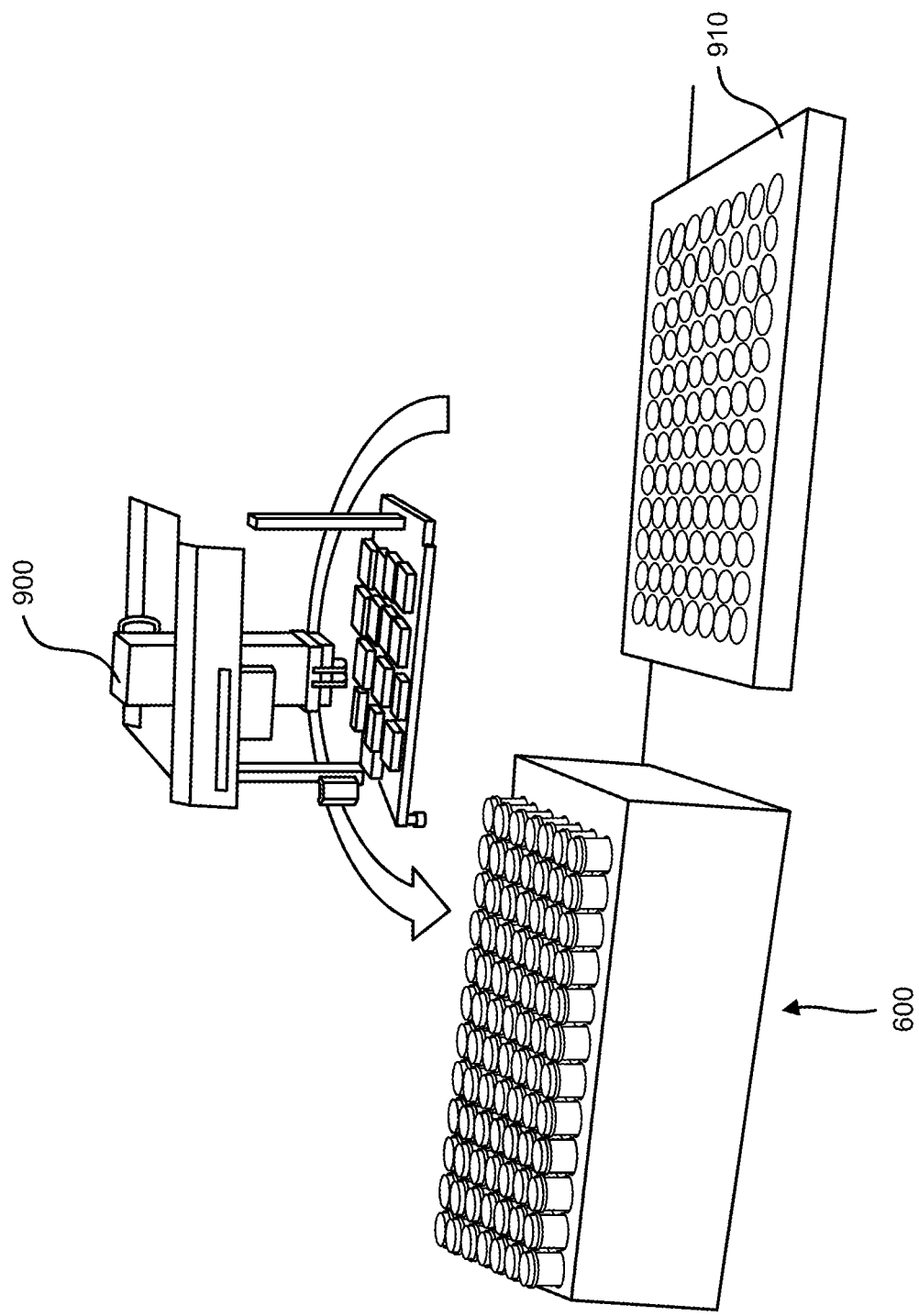
FIG. 9 illustrates a liquid handler for transferring samples into the detection system of FIG. 6.

The sample can be placed in the sample wells by hand or by a liquid handler. FIG. 9 illustrates an exemplary liquid handler 900 for transferring samples into the vials of a detection system. The liquid handler 900 can transfer one or more electrolytes and analyte samples into the sample well (e.g., from a microtiter plate 910 to the vials of the detection system).

The detection system detects a potential associated with the sample (e.g., via the reference electrode) and the feedback circuit (e.g., feedback circuit in the readout channel) provides a feedback control signal (e.g., via the counter electrode) to the sample. The feedback control signal can suppress voltage noise of the sample. The voltage noise can be representative of energy fluctuations in the sample (e.g., in the vicinity of an interface between the electrolyte and a working electrode). This can result in efficient resonant charge transfer between, for example, the electrolyte-dissolved redox species and the working electrode (e.g., charge transfer between discrete electronic energy levels of vibration-dressed electronic states in the redox species and energy levels in the working electrode). The feedback control signal can limit the multiple scattering contributions from the environment which can result in resonant charge transfer.

An analyte in the sample can be detected from working electrode current indicative of the analyte dependent resonant charge transfer process at the working electrode. The feedback circuit can detect the current at the working electrode and digitize the feedback current information (e.g., using an analog to digital converter). The feedback current information can be compared with information related to the effects of various analytes on charge transfer process (e.g., information stored in a database).

Figure 10:
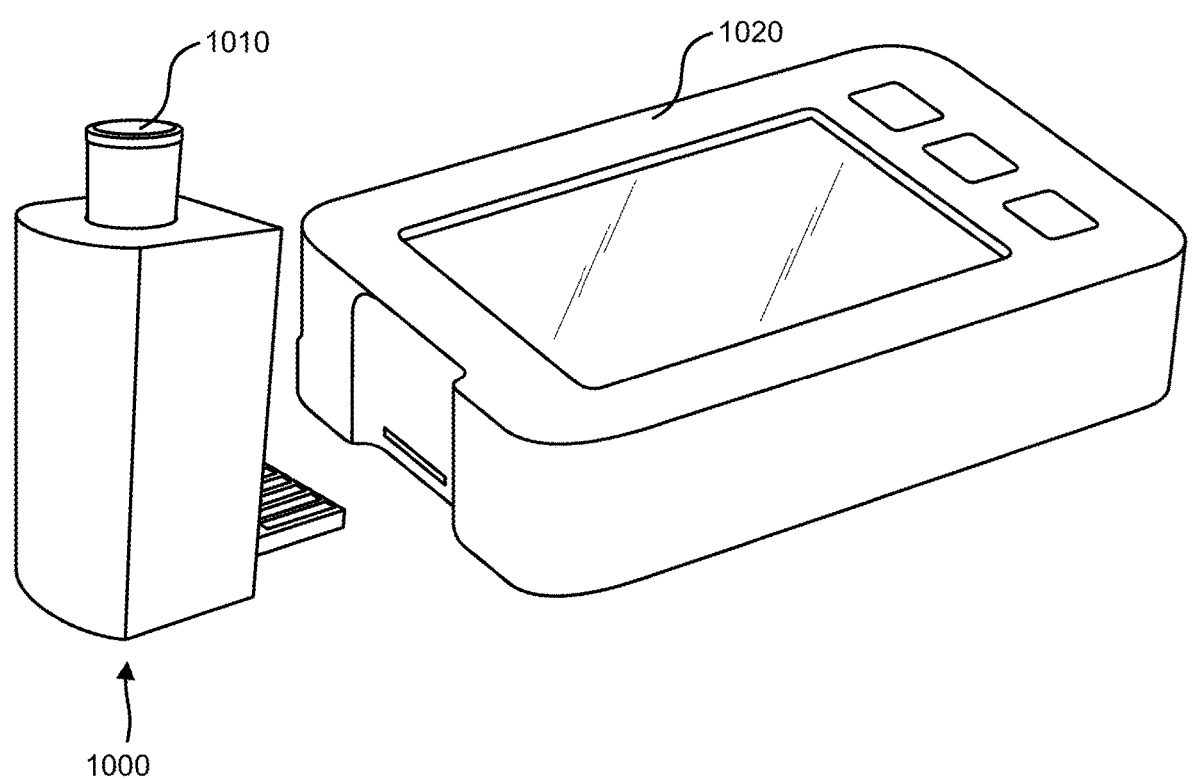
FIG. 10 illustrates a point-of-care detection system.

FIG. 10 illustrates a point-of-care detection system 1000. The point-of-care detection system can have a sensing module that can couple with a vial 1010 (e.g., vial 602), for example, by a mechanical socket. The mechanical socket can ensure that electrical connection between the electrodes of the vial and the electrodes of the sensing module is robustly established. The detection system 1000 can include a contact fixture and a readout channel. Because the detection system 1000 has a single sensing module, the detection system 1000 may not include a switching matrix. The detection system 1000 can communicate with a readout and computing device 1020 (e.g., via a data pin, by short-range wireless communication). For example, the detection system 1000 can be plugged into the computing device 1020.

Figure 11:
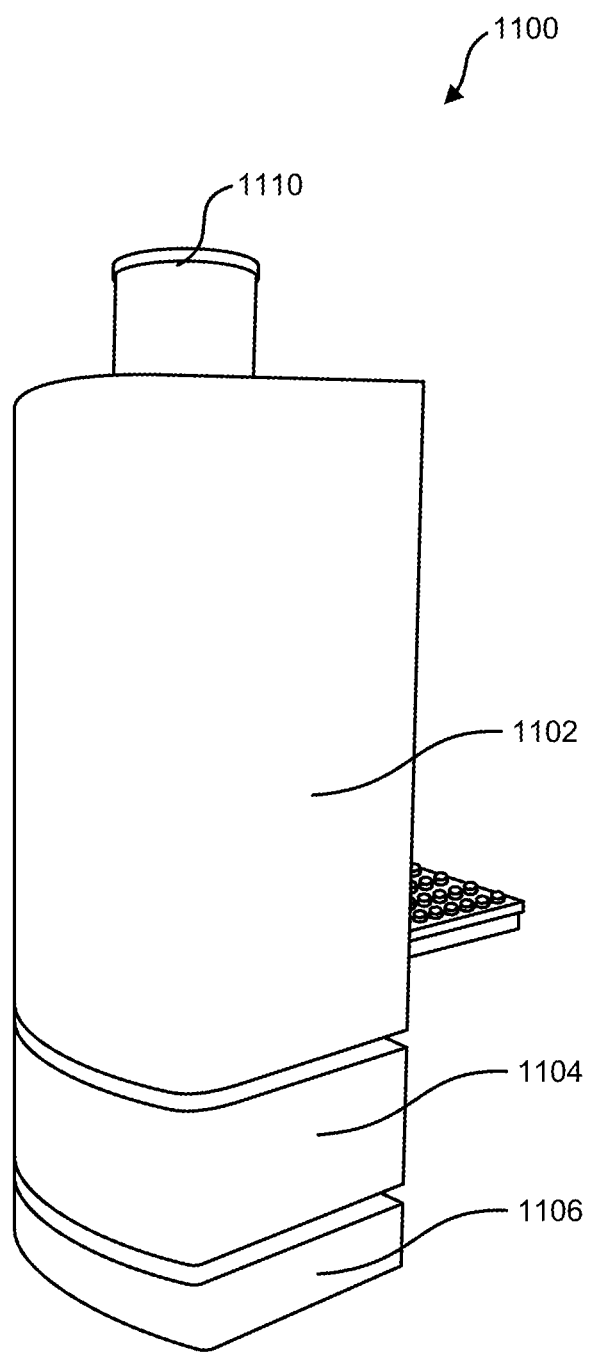
FIG. 11 illustrates an exemplary stand-alone detection system.

FIG. 11 illustrates an exemplary stand-alone detection system 1100. The stand-alone detection system 1100 can include a sensing system 1102, a communication system 1104 and a power delivery system 1106. The sensing system 1102 can be configured to couple to a vial 1110. In some implementations, the vial 1110 can be mechanically integrated with the sensing system 1102. In some implementations, the vial 1110 can be slid into the sensing system 1102. The vial 1110 can include electrodes that can couple to a sample that can be received by the vial 1110. For example, the electrodes of the vial 1110 can operate as counter electrode, working electrode and reference electrode (e.g., as described in reference to vials 602, 702, etc.).

The sensing system 1102 can include a low-noise feedback system (e.g., low-noise feedback system described in Provisional Application No. 62/328,798 and PCT Application Serial No. PCT/US2017/29854, which are incorporated herein by reference in its entirety) that can detect analytes in the sample received by the vial 1110. The feedback system can electrically couple to electrodes of the vial 1110. The sensing system 1102 can include a camera that can be used to track individual vial units (e.g., for quality control purposes). For example, the camera can be an optical code reader that can detect a bar code (e.g., bar code on the vial 1110). The bar code can be associated with the sample in the vial 1110, and the detected bar code can be indicative of the sample and/or individual vial unit in the vial 1110.

The communication system 1104 can be in communication with the sensing system. The communication system 1104 can receive analyte data detected by the sensing system 1102, bar-code data detected by the camera (see FIG. 13), etc. The communication system 1104 can include a microcontroller unit that can transmit data (eg., analyte data, bar-code data, etc.) to an authorized computing device (e.g., computer, tablet, cellphone, etc.), a server, etc. In some implementations, the data can be transmitted to an intermediate gateway (or a user interface in the authorized computing device) and/or an external server (e.g., a cloud). The computing device/server can verify data received from the communication system 1104, and can perform additional data analysis.

The data can be transmitted wirelessly (e.g., via WiFi, Bluetooth, and the like), and/or via serial ports (e.g., USB) (e.g., between the communication system 1104 and the intermediate gateway, between intermediate gateway and a cloud server, etc.) An authorized user can access the transmitted data via a secured connection. A network of multiple stand-alone detection systems 1100 (e.g., network of 96, 384, etc., detection systems) can perform multiple detections (e.g., simultaneously). Such a network can result in a high throughput analyte detection system.

The power delivery system 1106 can include a power source (e.g., a removable battery) to provide energy to the sensing system 1102, communication system 1104, etc. The stand-alone detection system 1100 can be modular. For example, the sensing system 1102, the communication system 1104 and the power delivery system 1106 can be assembled together to form the detection system 1100 and can be disassembled (e.g., after analyte detection).

Figure 12:
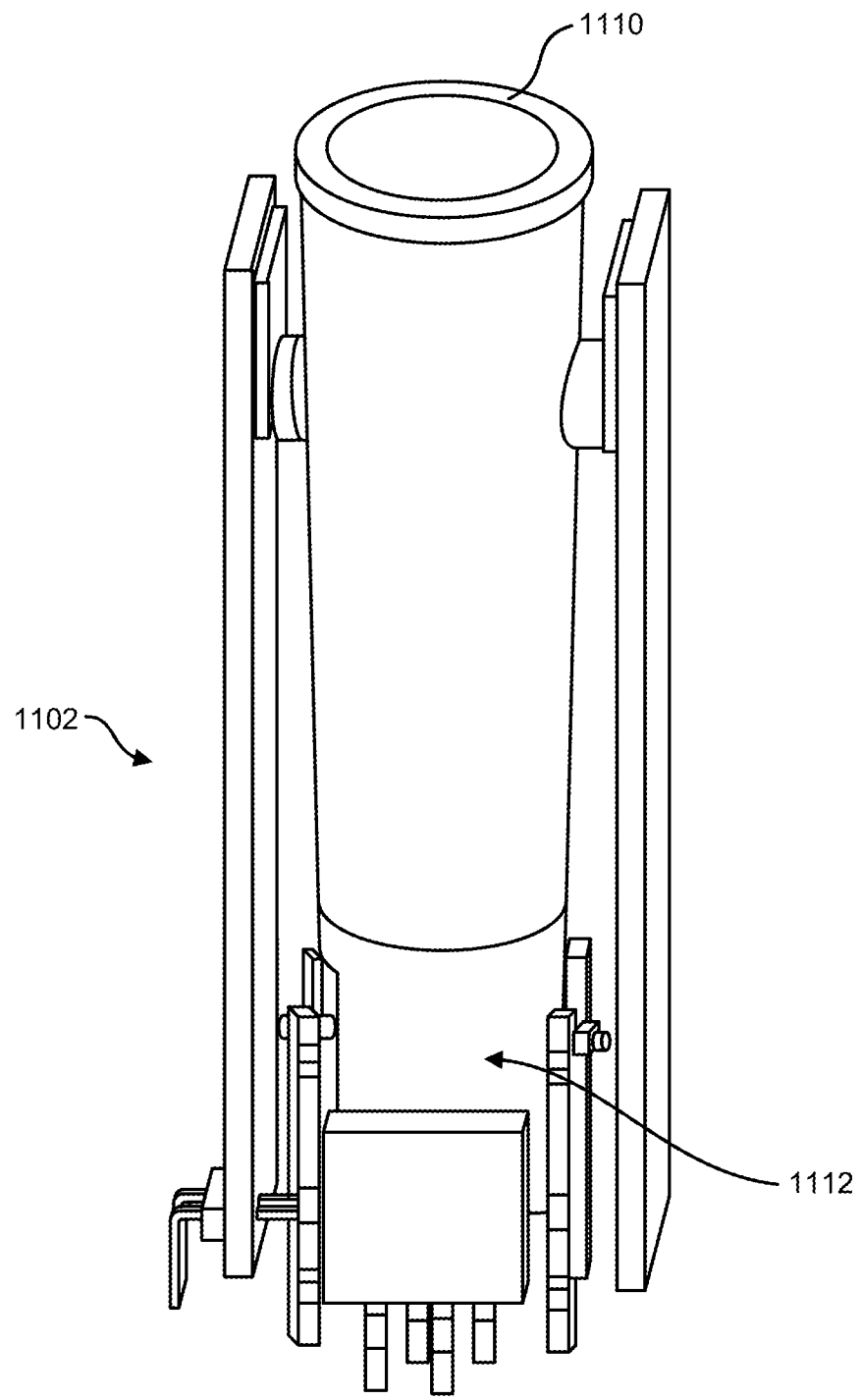
FIG. 12 illustrates coupling between a vial 1110 and a sensing system in the stand-alone detection system in FIG. 11.
Figure 13:
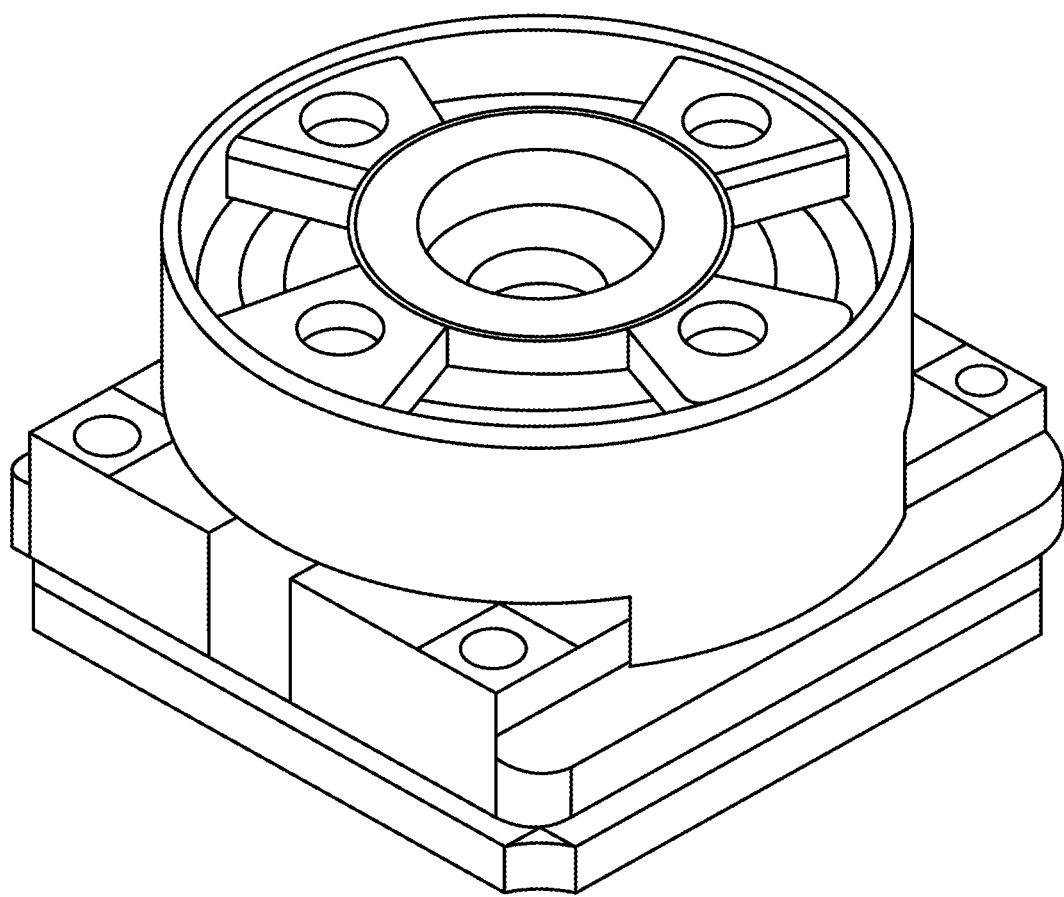
FIG. 13 illustrates an exemplary camera that can be integrated with the stand-alone detection system of FIG. 11.

FIG. 12 illustrates coupling between the vial 1110 and the sensing system 1102. Portion of the sensing system at a distal end 1112 of the vial 1110 can include a feedback circuit and/or a camera. FIG. 13 illustrates an exemplary camera that can be integrated into the sensing system 1112 (or in the distal end of the vial 1110).

Working Example

A sensing module with a feedback circuit detects biomolecular analytes within a complex clinical sample like whole blood in an electrolyte containing the potassium ferri-/ferro-cyanide redox couple. The concentration of the analyte in the electrolyte ranges from 1 pg/ml (picogram/milliliter) to 1 mg/dl (milligram/deciliter). The sensing module includes a counter electrode, a reference electrode and a working electrode that are in electrical contact with the electrolyte. The counter, reference and working electrodes are made of metals (e.g., gold, platinum, platinum-iridium, silver, silver/silver-chloride). The sensing module detects the potential of the redox active species in the electrolyte at the reference electrode, and based on the detected potential, provides a low-noise high gain feedback current signal to the electrolyte via the counter electrode. The charge in the current signal is carried between the counter electrode and the working electrode by phosphate and cyanide anions and potassium cations.

Choice of metals for the electrodes leads to electrochemical stability for potentials ranging from −1 volt to 1 volt. For example, gold and platinum electrodes enable thin film chemistry functionalization, like a self assembled film comprising 1-propanethiol. The portion of the counter electrode immersed in the sample has an area of about 0.5 $cm^2$ to about 1 $cm^2$. The working electrode has an area of about 2500 $nm^2$. The distance between the aforementioned portion of the counter electrode and a working electrode in the chip scale sensor ranges from about 0.5 cm to about 1 cm. Volume of the redox species ranges from 0.5 ml to 1 ml. Volume of the analyte sample (containing analyte to be detected) ranges from 1 μl (microleter) to 10 μl. The horizontal extent of the sensing module can be approximately 9 mm and the vertical extent of the sample well can be approximately 15 mm.

A key component to the biosensor according to embodiments described herein is analog front-end instrumentation, which is relied upon to achieve minimum noise in an acquired signal. Physical and electronic sources of noise in a measured transition rate limit the extent of decoupling achievable and can become measurement-limiting when transition rates in the weakly-coupled regime are on the order of 10 fA. As stated earlier, scaling down the active electrode area supplements electronic decoupling achieved by engineering the nano-scale, information transducing interface, and simultaneously miniaturizes the sensing platform. Similarly, noise in the system also limits the extent to which the electrode area can be minimized. In sum, to achieve effective device minimization, rapid analyte identification, and battery life preservation, non-electron transfer leakage currents and noise in the acquisition electronics should preferably be minimized.

A measured non-adiabatic current is a function of two non-interacting frequency domains: (a) a "macro-frequency" (approximately 1 Hz) that determines the rate-limiting step in the macroscopic electrochemical system and (b) a "micro frequency" (>1012 Hz) that measures the dynamics of molecular vibrations, where the dynamics are manifest in the electronic energy, or applied bias, space. A low-frequency Alternating Current (AC) excitation is applied to the electrochemical interface, and the current is recorded as a function of Direct Current (DC) bias at the electrode. The non-adiabatic transition rate is contaminated, at least in part, by bandlimited white noise and electromagnetic interference. Effective signal extraction requires suppression of both extrinsic and intrinsic noise contributions. In short, because of the low frequency transition signal strength, a high signal-to-noise ratio is preferable.

Figure 14:
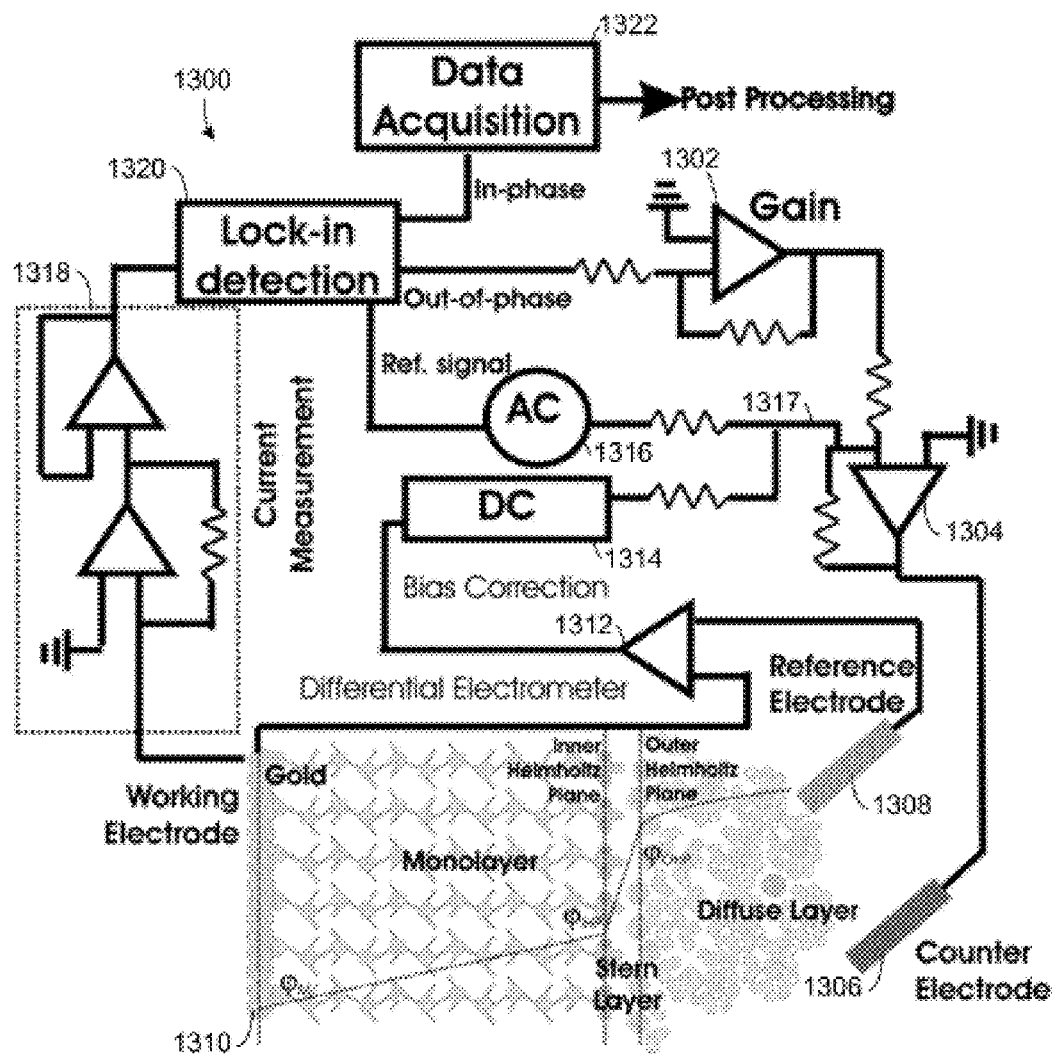
FIG. 14 shows an example of three-electrode feedback suppression of thermal noise for electronic transition measurement.

FIG. 14 shows an example of three-electrode feedback suppression of thermal noise for electronic transition measurements. In one embodiment, a three-electrode analog measurement topology circuit 1300 is used for high gain feedback suppression of voltage-noise in the macro-frequency domain. The circuit 1300 includes a first gain amplifier 1302, a second gain amplifier 1304 coupled to an output of the first gain amplifier 1302, and a counter electrode 1306 coupled to an output of the second gain amplifier 1304. The circuit 1300 further includes a reference electrode 1308 and a working electrode 1310, each coupled to a bias amplifier 1312. An output of the bias amplifier 1312 is coupled to a DC generator 1314. Outputs of the DC generator 1314 and an AC generator 1316 are combined at a node 1317 in the circuit 1300 and provided as an input to the second gain amplifier 1304. As illustrated in FIG. 14, the combined outputs of the DC and AC generators 1314 and 1316 are further combined with the output of the first gain amplifier 1302 at the node 1317 before being provided as input to the second gain amplifier 1304.

The circuit 1300 further includes a current measurement circuit 1318 coupled to the working electrode 1310, and a lock-in detection circuit 1320 coupled to an output of the current measurement circuit 1318. As illustrated in FIG. 14, a reference signal output of the lock-in detection circuit 1320 is provided as an input to the AC generator 1316, an out-of-phase signal output of the lock-in detection circuit 1320 is provided as an input to the first gain amplifier 1302, and an in-phase signal output of the lock-in detection circuit 1320 is provided as an input to a data acquisition element 1322 for processing.

According to one embodiment, a feedback loop of the circuit 1300 acts to minimize thermal noise on the order of pA/Hz1/2, at room temperature. In embodiments that have tunneling transition currents on the order of 10 fA, noise on the order of 2 fA rms/Hz1/2 would be sufficient for the resolution of spectral features in measured data.

Sensing of the low frequency modulated energy state transition signal may be performed with low noise current amplification and readout circuitry. The signal acquisition path employs chopper modulation to mitigate flicker noise from CMOS devices, which may be expected to be significant around the "macro" frequency modulation. In one embodiment, a metal-oxide-semiconductor-field-effect transistor (MOSFET) that comprises defect free or substantially defect so free oxide interfaces along a channel region is relied upon. This eliminates the trapping and detrapping of carriers that create 1/f noise characteristics.

What is claimed is:

1. A method of detecting analytes comprising:
   detecting a potential associated with a sample received in a sample well by a first electrode;
   generating a feedback signal by a feedback circuit electrically coupled to the first electrode; and
   providing the feedback signal to the sample via a second electrode, the feedback signal configured to provide excitation control of redox species in the sample at a third electrode,
   wherein the first, the second and the third electrodes are coupled to a platform configured to receive the sample well.

2. The method in claim 1, wherein the feedback circuit is configured to detect a current from the sample via the third electrode, the detected current indicative of an analyte in the sample.

3. The method in claim 2, wherein the first electrode and the third electrode are located on a sensor.

4. The method in claim 3, wherein the platform comprises an electromagnetic shield configured to shield the sensor by attenuating external electromagnetic radiation.

5. The method in claim 2, wherein the first electrode is located on a cap configured to removably couple to the sample well.

6. The method in claim 2, wherein the first electrode is mounted on a wall of the sample well.

7. The method in claim 1, wherein the second electrode comprises a first end and a second end, the first end is coupled to the platform and the second end is configured to electrically connect with the sample in the sample well.

8. The method in claim 7, wherein the second end comprises a surface configured to extend across the sample well, the surface and the platform substantially parallel to each other.

* * * * *